US008464714B2

(12) United States Patent
Chalvignac

(10) Patent No.: US 8,464,714 B2
(45) Date of Patent: Jun. 18, 2013

(54) BREATHING ASSISTANCE DEVICE COMPRISING A GAS REGULATING VALVE AND ASSOCIATED BREATHING ASSISTANCE METHOD

(75) Inventor: Phillippe Chalvignac, Hunters Hill (AU)

(73) Assignee: ResMed Paris (FR)

( * ) Notice: Subject to any disclaimer, the term of this patent is extended or adjusted under 35 U.S.C. 154(b) by 1016 days.

(21) Appl. No.: 11/919,382

(22) PCT Filed: May 2, 2005

(86) PCT No.: PCT/IB2005/001454
§ 371 (c)(1),
(2), (4) Date: Jun. 10, 2009

(87) PCT Pub. No.: WO2006/117591
PCT Pub. Date: Nov. 9, 2006

(65) Prior Publication Data
US 2010/0018529 A1 Jan. 28, 2010

(51) Int. Cl.
*A61M 16/20* (2006.01)
*A61M 2016/27* (2006.01)

(52) U.S. Cl.
USPC .................................. 128/204.26; 128/205.24

(58) Field of Classification Search
USPC ........................... 128/204.26, 201.28, 205.24
See application file for complete search history.

(56) References Cited

U.S. PATENT DOCUMENTS 1,990,130 A * 2/1935 Moos ....................... 128/201.28
3,429,552 A * 2/1969 Erickson et al. ......... 251/129.17
3,831,596 A * 8/1974 Cavallo .................... 128/204.23
4,318,399 A * 3/1982 Berndtsson .............. 128/204.23
4,336,590 A * 6/1982 Jacq et al. ................ 128/204.21
4,344,144 A * 8/1982 Damico et al. ................ 700/282
4,494,537 A * 1/1985 Gottlieb ................... 128/204.26
4,611,591 A * 9/1986 Inui et al. ................. 128/205.24
4,798,689 A * 1/1989 Heim et al. .................. 261/39.1
4,903,693 A * 2/1990 Yasue ...................... 128/203.12
4,928,684 A * 5/1990 Breitenfelder et al. .. 128/204.21
4,971,108 A * 11/1990 Gottlieb ........................ 137/495
5,273,031 A * 12/1993 Olsson et al. ............ 128/204.18
5,305,739 A 4/1994 Gray (Continued)

FOREIGN PATENT DOCUMENTS

EP 0 615 764 A1 9/1994
EP 0 990 448 A2 4/2000

(Continued)

OTHER PUBLICATIONS

Translation of Official Office Action JPA 2008-509440.

*Primary Examiner* — Stephen Crow
(74) *Attorney, Agent, or Firm* — Lerner, David, Littenberg, Krumholz & Mentlik, LLP

(57) ABSTRACT

The invention relates to a breathing assistance device for a patient (P), the device including: —a source of respiratory pressurized gas (S), a gas transmission duct (31) comprising a distal end (31*d*) coupled to said source and a proximal end (31*p*) coupled to the patient, —a gas regulating valve (32, 50) interposed in the gas transmission duct at a proximal location, comprising a leakage orifice (531) and an obstruction means (54) capable of varying the opening of the leakage orifice upon signal of controlling means (35) and allowing a bidirectional gas flow through the leakage orifice in both expiration and inspiration phases.

18 Claims, 24 Drawing Sheets

U.S. PATENT DOCUMENTS

| | | | | |
|---|---|---|---|---|
| 5,339,807 | A | 8/1994 | Carter | |
| 5,398,673 | A | 3/1995 | Lambert | |
| 5,398,676 | A * | 3/1995 | Press et al. | 128/204.23 |
| 5,400,777 | A * | 3/1995 | Olsson et al. | 128/204.18 |
| 5,484,270 | A | 1/1996 | Adahan | |
| 5,787,882 | A | 8/1998 | Hamilton | |
| 6,024,088 | A * | 2/2000 | Ishikawa et al. | 128/204.21 |
| 6,029,660 | A * | 2/2000 | Calluaud et al. | 128/203.12 |
| 6,371,110 | B1 * | 4/2002 | Peterson et al. | 128/202.27 |
| 6,443,154 | B1 | 9/2002 | Jalde et al. | |
| 6,990,977 | B1 * | 1/2006 | Calluaud et al. | 128/203.12 |
| 7,201,166 | B2 * | 4/2007 | Blaise et al. | 128/203.12 |
| 7,273,052 | B2 * | 9/2007 | Gossweiler | 128/206.26 |
| 7,552,731 | B2 * | 6/2009 | Jorczak et al. | 128/205.24 |
| 7,658,786 | B2 * | 2/2010 | Lin | 95/96 |
| 7,681,573 | B2 * | 3/2010 | Matthiessen et al. | 128/204.18 |
| 7,753,049 | B2 * | 7/2010 | Jorczak et al. | 128/205.24 |
| 7,779,834 | B2 * | 8/2010 | Calluaud et al. | 128/203.12 |
| D631,542 | S * | 1/2011 | DeGross et al. | D24/129 |
| 2004/0069305 | A1 | 4/2004 | Niemela et al. | |
| 2004/0194783 | A1 | 10/2004 | McAuliffe et al. | |
| 2008/0092891 | A1 * | 4/2008 | Cewers | 128/204.18 |
| 2010/0282251 | A1 * | 11/2010 | Calluaud et al. | 128/200.23 |

FOREIGN PATENT DOCUMENTS

| | | | |
|---|---|---|---|
| EP | 1 059 096 | A2 | 12/2000 |
| EP | 1 197 238 | A2 | 4/2002 |
| WO | 98/26830 | A1 | 6/1998 |
| WO | 02/23678 | A1 | 3/2002 |

* cited by examiner

BREATHING ASSISTANCE DEVICE COMPRISING A GAS REGULATING VALVE AND ASSOCIATED BREATHING ASSISTANCE METHOD

The present patent application is a non-provisional application claiming the benefit of International Application No. PCT/IB 2005/001454, filed May 2, 2005.

FIELD OF THE INVENTION

The present invention relates to a breathing assistance device for a patient.

More precisely, the invention relates to a breathing assistance device for a patient breathing in successive respiratory cycles, each respiratory cycle being defined by at least an inspiration phase and at least an expiration phase.

TECHNICAL BACKGROUND

A variety of breathing assistance devices, which we will also generally refer to as "respirators" in this text, are available today.

These respirators are equipped with a source of respiratory pressurised gas. They are qualified as "autonomous" as an external pressurised gas feeding is not required to operate them.

These devices provide the patient, at each inspiration, with a respiratory gas (typically ambient air to which a complementary gas such as oxygen can be added).

Different types of respirators are known. These different types of respirators can be classified e.g. according to their size.

Indeed, the size of these devices is an important parameter: it is generally desirable to minimize this size, in order to facilitate the operation of a same and single device in varied places and circumstances (e.g. home, as well as hospital), and in order to increase the mobility of the patient.

Non-Transportable Devices

A first type of respirators relates to the ones qualified as being non-transportable. This first type is schematically illustrated trough FIGS. 1*a* to 1*d*.

Such devices are generally equipped with a respiratory gas source S1 having a very large size and/or weight. This gas source can be internal to the device, located in this case in a central unit 10, as the non-transportable respirator described hereinafter and illustrated in FIGS. 1*a* to 1*d*. The gas source can also be external to the device.

In these devices, the source of gas is coupled to the patient P through two ducts, an inspiration duct 11 dedicated to the inspiration phase and through which the patient P inspires the pressurised gas from the source of gas, and an expiration duct 12 dedicated to the expiration phase and through which the patient can expulse expiratory gases, such as carbon dioxide.

These non-transportable respirators are further provided with an inspiratory valve 13 and an expiratory valve 14. These two valves are located close to the gas source S1, respectively on the inspiration duct 11 and on the expiration duct 12.

The inspiratory valve 13 allows controlling the flux of the pressurised gas transmitted to the patient during the respiratory phases.

The expiratory valve 14 allows the expiratory gases of the patient to be rejected out of the expiratory duct 12, in the surrounding atmosphere. For this purpose, the expiratory valve can further be controlled with a PEP (Positive Expiratory Pressure).

Most of the operating modes of the respirators require a monitoring of the expiratory gas flow and/or expiratory pressure. Therefore sensor(s) 19 for sensing the gas flow and/or pressure have to be provided in the respirator.

Each sensor usually needs to be connected to the central unit 10 of the respirator by at least three wires, in order to be power supplied and for conveying data information.

Therefore the sensors 19 are generally located near the gas source S1 in order to avoid further increasing the complexity of the already quite complex and large double transmission circuit by the addition of sensors and wires.

If it is desired that the sensors 19 are located in the vicinity of the expiratory valve, said expiratory valve 14 has thus to be located close to the gas source S1.

Both the inspiratory and expiratory valves require specific and often complex controlling means 15 in order to be operated properly.

The non-transportable respirators are generally provided with relatively long ducts, of about 150 to 180 cm.

This configuration implies a breathing resistance which goes against the easy expiration of the patient.

Indeed, if the expiratory valve 14 is located at the end of the expiration duct 12 near the gas source S1 (distal end), and the expiration duct 12 being relatively long, the patient P will need to "push" his expiration through the expiration duct 12 until the expired air reaches the expiration valve to be rejected in the atmosphere.

Transportable Respirators

A second type of respirators can be referred to as transportable respirators, as schematically illustrated in FIGS. 2*a* to 2*d*. This type of transportable respirator is provided with a central unit 20 comprising an internal respiratory gas source S2.

The gas source S2 may be a small turbine, having optimised characteristics in order to limit the volume occupied by the device.

A further way to limit the volume of these devices is to use a single gas transmission duct 21 between the source S2 and the patient P, in contrast with devices having two ducts (an inspiration duct and an expiration duct).

The operation principle of these respirators is based on the use of an expiratory valve 22 located on the single duct 21, near the patient P (i.e. at the proximal end of the duct).

Such proximal localisation of this expiratory valve 22 allows, in particular during the expiratory phase, to avoid the breathing resistance phenomenon which would be caused by the length of the duct used for expiration if the expiratory valve was located at the distal end of the duct.

In the known transportable respirators, such as represented in FIGS. 2*a* to 2*d*, this expiratory valve 22 is a pneumatic valve being operated thanks to a pressurised air feeding conduit 23, coupled with the respiratory gas source S2 (or to another source of pressure such as an independent microturbine), and which inflates an obstructing cuff 24 of the expiratory valve 22.

Such control of the expiratory valve thus requires a specific conduit 23, which limits the miniaturization of the respirator.

During the expiration phase, the expiratory valve 24 is either opened or partially closed in order to establish a positive expiratory pressure (PEP) in the gas transmission duct to balance the residual overpressure in the patient lungs.

In order to establish such a PEP, it is necessary to control very precisely the pneumatic inflating pressure of the cuff 24 of the expiratory valve 22 This increases the complexity of the controlling means 25 of the respirator.

In some respiratory modes, the expiratory valve has to be operated as much as possible in real time, which is quite difficult in such expiratory valves because of the pneumatic inertias which are associated to them.

Moreover the configuration of such a known respirator imposes a limitation of the value of, the PEP at around 20 mBar, while some respiratory modes would need a higher value of the PEP (e.g. 40 mBar or even more).

For the same reason as for non-transportable respirators, the expiratory gas flow and/or expiratory pressure may have to be controlled and gas flow and/or pressure sensors 29 have therefore to be provided near the expiratory valve 22.

Here again this requires providing wires along the gas transmission duct 21 between the central unit 20 containing the gas source S2 and the patient P (namely three wires—two for power supply and one for data transmission—for each pressure sensor, and two power supply wires for each gas flow sensor). Since expiratory gas flow and pressure generally have to be measured, a connection cable 26 of at least five wires is thus required between the central unit 20 and the expiratory valve 22 at the proximal end of the device.

Comment on Situation of Disabled Control of the Expiratory Valve

In order for the patient to securely use a respirator, the latter being transportable or not, this device must of course allow the patient to breathe in any situation, including if the pressurised gas source is disabled (breakdown or other). There are therefore security standards to fulfil so that the breathing assistance device can work even if the gas source is disabled.

Thus, with a respirator having a single gas transmission duct 21 as described before and a specific conduit 23 for pneumatic control of the expiratory valve 22, the patient P can always expires through the pneumatic expiratory valve 22, even if the pneumatic feeding of the expiratory valve 22 is disabled, as shown in FIG. 2*d*.

Indeed, if the pneumatic feeding of the expiratory valve is disabled, (this being the case when the gas source is disabled, if the source provides the control of the valve), the cuff 24 of the expiratory valve 22 will not be fed anymore, preventing therefore the PEP control, but still allowing the patient P to reject the expiratory gases $E_P$ through the expiratory valve 22.

In such case, it will however be impossible for the patient P to inspire through this pneumatic expiratory valve 22, since the cuff 24 shall obstruct the passage between the inside and the outside of the transmission duct 21, because of the patient inspiration $I_P$.

Consequently, transportable respirators as illustrated in FIGS. 2*a* to 2*d* comprise a security back flow stop valve 27 near the gas source S2. As represented in FIG. 2*a*, this security valve 27 will normally be closed under the effect of the pressure feeding $G_S$ coming from the gas source S2, but if the latter is disabled, the pressure of the patient inspiration $I_P$ will open the security valve 27, allowing the patient P to inspire air from outside, as illustrated in FIG. 2*c*.

The disabling of the gas source S2 corresponds to a particular case of disabling of the pneumatic control of the expiratory valve 22. It is specified that in this text such disabling of the gas source S2 is understood as more generally referring to a disabling of the pneumatic control of the expiratory valve 22.

In order to allow a safe inspiration through the security valve 27 and the whole length of the duct 21, the diameter of the duct will have to be large.

It is specified in this respect that there are generally pressure loss standard requirements to fulfil for addressing this issue of safety. For example, the French standards state that the maximum pressure loss between the source and the patient must not exceed 6 hPa for 1 liter·second for an adult and 6 hPa for 0.5 liter·second for a child.

And in order to fulfil such requirements, the transmission duct of known devices such as illustrated in FIGS. 2*a* to 2*d* must have a minimum diameter of 22 mm for an adult and a minimum diameter of 15 mm for a child.

Such large diameter of the duct is of course an obstacle to miniaturization of the device.

For a non transportable respirator (see FIGS. 1*a* to 1*d*), the patient P will always be able to expire through the expiration duct 12, even if the gas source S1 is disabled, as shown in FIG. 1*d*.

If the gas source S1 is disabled, as illustrated in FIG. 1*c*, the inspiration phase is made possible through a security back flow stop valve 16 located on the inspiration duct 11, near the gas source S1.

This security back flow stop valve 16 is not located on the expiration duct 12 as it would be dangerous for the patient P to inspire through the expiratory duct 12 which contains a plug of carbon dioxide.

For the same reasons as for the transportable respirators, the diameters of the duct must be relatively large to fulfil the pressure loss requirements, that is a least 15 mm for children and 22 mm for adults, in order to allow a safe inspiration through the security valve 16.

And here again, such large diameter is an obstacle to miniaturization.

Comment on Ability to Operate According to Different Modes

In addition, it is to be noted that the pathologies and diseases to be treated by the respirators are varied, and the breathing assistance devices can therefore be of different types, such as the barometric or volumetric ones, and be operated according to different operating modes.

Each operating mode is defined by particular setting and checking variables but also by a particular type of material.

Some devices, which can be referred to as hybrid, are able to work according to several operating modes. However their material configuration, in particular the accessories (as the type of ducts between the gas source and the patient, the presence or not of an expiratory valve, the use of a mask with apertures, etc.), must be adapted to the chosen operating mode. And it would be desirable to operate a same and single device according to a large variety of modes, without requiring adapting the device (i.e. adapting its ducts, accessories, etc.).

The above being exposed, it is an object of the invention to allow further miniaturization of the devices.

In this respect, it is a particular object of the invention to allow reduction of the diameter of the duct between the source and the patient, while fully respecting the safety requirements.

It is another object of the invention to obtain a configuration which is as simple as possible, in particular by reducing the number of wires between the central unit of the respirator and the proximal end of the duct.

It is another object of the invention to allow an actual real-time control of the device—in particular of its gas regulation valve.

It is another object of the invention to allow operating different modes with a same respiratory device, without requiring adapting the device.

And more generally, it is an object of the invention to address the limitations and drawbacks mentioned above in this text.

SUMMARY OF THE INVENTION

In order to attain the above-mentioned objects, the invention proposes of a breathing assistance device as defined in claim 1.

In particular, the invention concerns a breathing assistance device for a patient breathing in successive cycles, each cycle being defined by at least an inspiration phase and at least an expiration phase, said breathing assistance device including:

- a source of respiratory pressurised gas,
- a gas transmission duct comprising a distal end coupled to said source and a proximal end coupled to said patient,
- a gas regulating valve comprising at least a leakage orifice between the inside and outside of said duct, and an obstruction means capable of varying the opening of said leakage orifice upon signal of a controlling means, characterised in that the gas regulating valve is interposed in said duct at a proximal location, and that the obstruction means is capable of allowing a bidirectional gas flow through said leakage orifice in both expiration and inspiration phases.

Preferable but not limited aspects of such a breathing assistance device are the following:

the obstruction means is electrically controlled, and the obstruction means may be an electromagnetic obstruction means;

the obstruction means includes a return means so that the leakage orifice remains at least partially opened in the absence of signal from the controlling means;

- the returns means is a magnetic equator;
- the electromagnetic obstruction means includes a metallic sheath wherein a coil is fixed, said coil being controllable by the controlling means and surrounding a movable magnetic element, the metallic sheath and the movable magnetic element defining the magnetic equator;
- the magnetic element comprises a toric magnet, a first polar piece and a second polar piece, said first and second polar pieces being coaxially fixed on either side of the toric magnet and being of different polarities, and said second polar piece comprising an obstruction piece being capable of obstructing the leakage orifice. The magnetic element is translatable along an axis of revolution of the toric magnet;
- the electromagnetic obstruction means may include two coaxial coils controllable by the controlling means, the first coil substantially surrounding the toric magnet and the first polar piece, and the second coil substantially surrounding the toric magnet and the second polar piece;
- the electromagnetic obstruction means is mounted coaxially relative to the gas transmission duct;
- the returns means is a compression spring;
- the electromagnetic obstruction means includes an armature surrounded by a coil, said coil being controllable by the controlling means, and said armature comprising an inner toric space wherein a magnetic element is translatable;
- the magnetic element is capable of obstructing the leakage orifice;
- the magnetic element is constraint by the compression spring;
- the magnetic element comprises a toric magnet and a magnet guide;
- the electromagnetic obstruction means is mounted transversally relative to the gas transmission duct.

Another aspect of the invention concerns a breathing assistance method for assisting a patient with a breathing assistance device of the invention, as defined in claim 17.

In particular, it concerns a breathing assistance method for assisting a patient with a breathing assistance device according to the invention, characterised in that the leakage orifice is at least partially opened in the absence of signal from the controlling means.

Preferable but not limited aspects of such a breathing assistance method are the following:

the leakage orifice is totally obstructed during inspiration phases whereas it is a least partially opened during expiration phases;

the leakage orifice, during expiration phases, is opened so that positive expiratory pressure (PEP) remains equal to expiration pressure of the patient;

the leakage orifice is totally opened in case of breakdown of the source of respiratory pressurised gas.

Finally, the invention relates to a gas regulating valve for a breathing assistance device, as recited in claim 25.

In particular, it relates to a gas regulating valve for a breathing assistance device, being interposed in a gas transmission duct of said breathing assistance device at a proximal location, and comprising at least a leakage orifice between the inside and outside of said duct, and an obstruction means capable of varying the opening of said leakage orifice upon signal of a controlling means, characterised in that the gas regulating valve is capable of allowing both an inward or an outward gas flow in both expiration and inspiration phases.

Preferable but not limited aspects of such a gas regulating valve are the following:

the obstruction means includes a return means so that the leakage orifice remains at least partially opened in the absence of signal from the controlling means;

the obstruction means is an electromagnetic obstruction means including a metallic sheath wherein a coil is fixed, said coil being controllable by the controlling means and surrounding a translatable magnetic element, the magnetic element comprising a toric magnet, a first polar piece and a second polar piece, said first and second polar pieces being coaxially fixed on either side of the toric magnet and being of different polarities, and said second polar piece comprising an obstruction piece being capable of obstructing the leakage orifice;

the obstruction means is an electromagnetic obstruction means including an armature surrounded by a coil, said coil being controllable by the controlling means, and said armature comprising an inner toric space wherein a magnetic element is translatable, the magnetic element being capable of obstructing the leakage orifice and being constraint by a compression spring.

BRIEF DESCRIPTION OF THE DRAWINGS

Other characteristics and advantages of the invention will become clear from the following description which is only given for illustrative purposes and is in no way limitative and should be read with reference to the attached drawings on which, in addition to FIGS. 1*a* to 1*d* and 2*a* to 2*d* which have already been commented above.

DETAILED DESCRIPTION OF THE DRAWINGS

Structure

General Structure of the Device

Figure 1A:
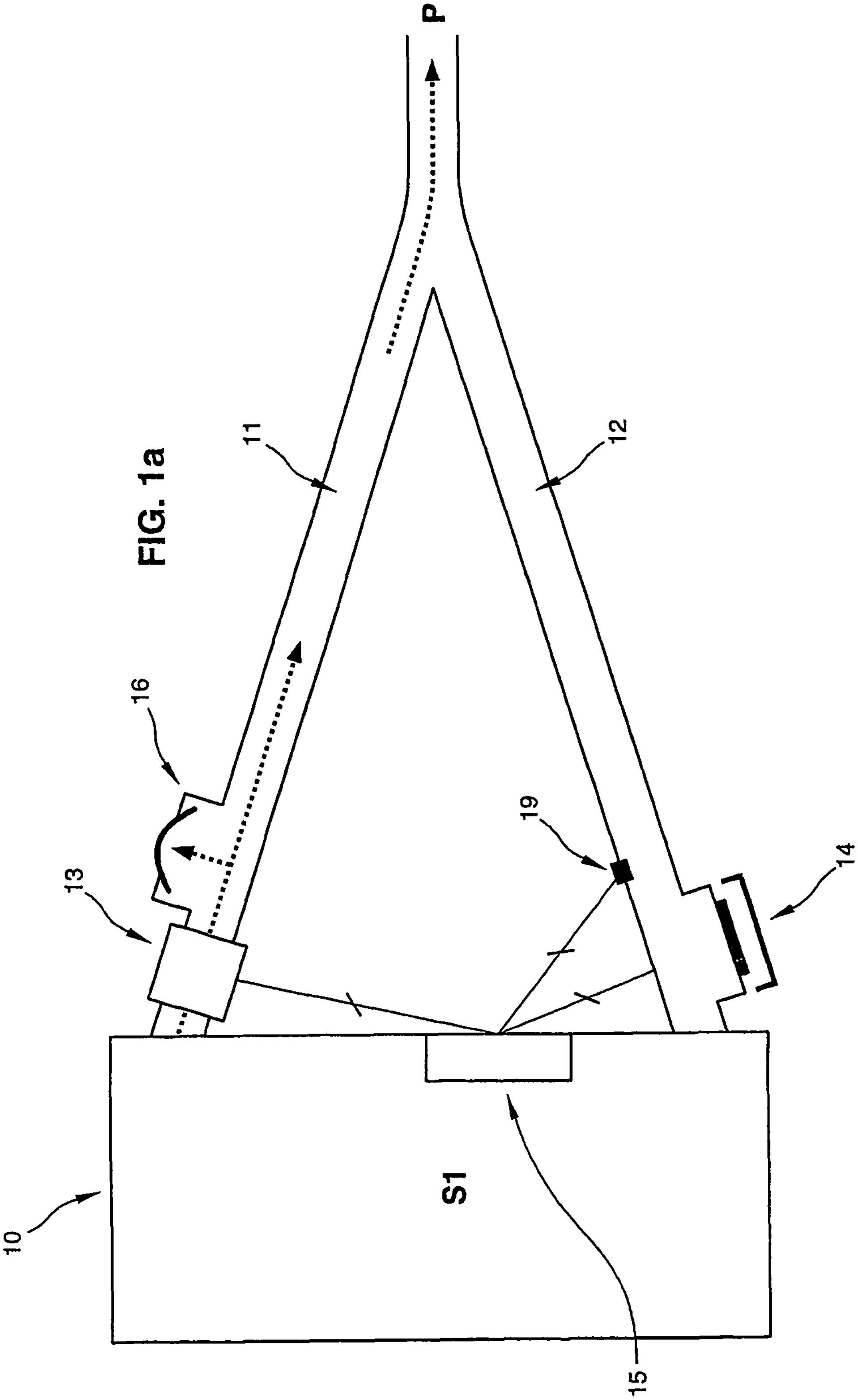
Figure 1B:
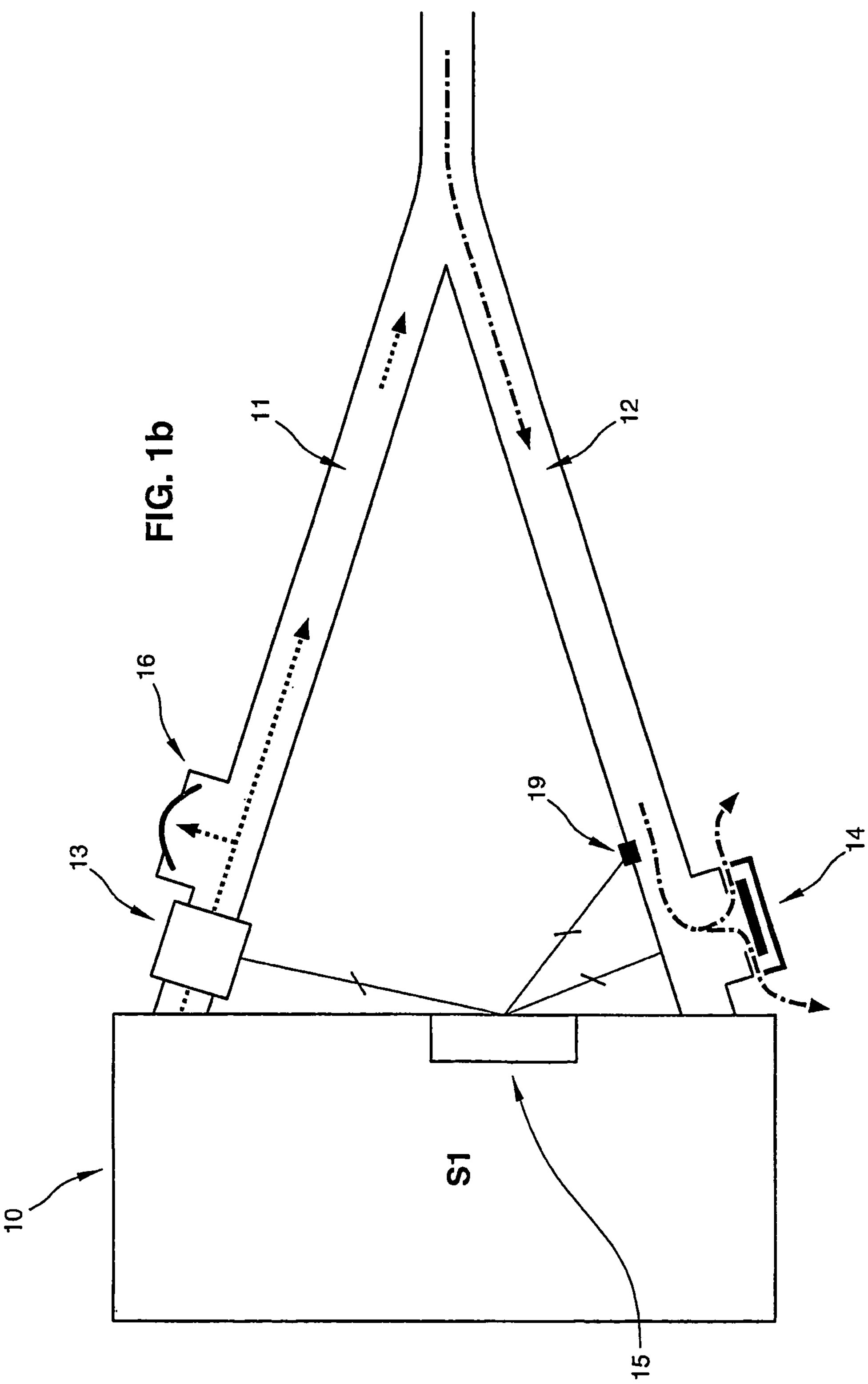
Figure 1C:
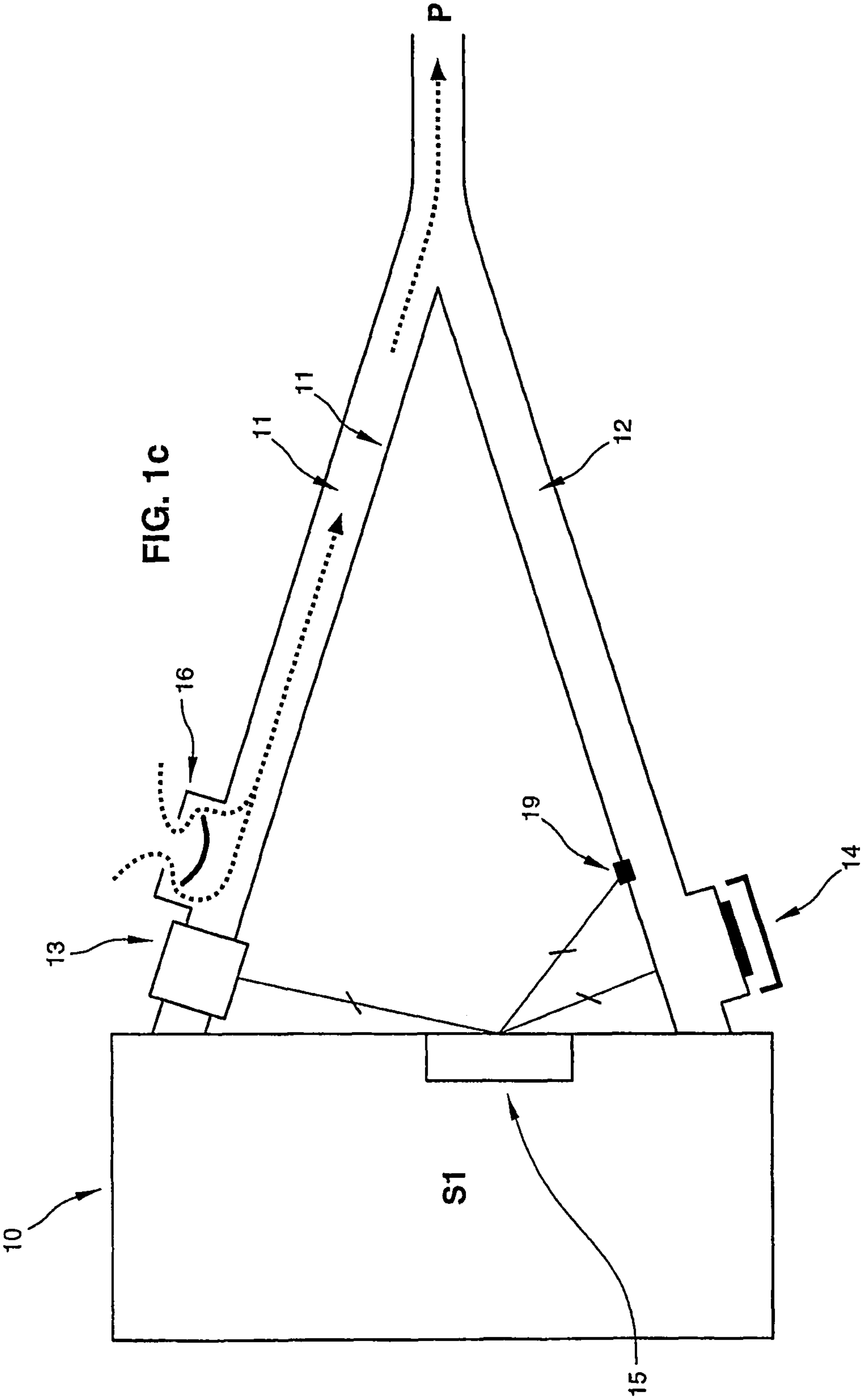
Figure 1D:
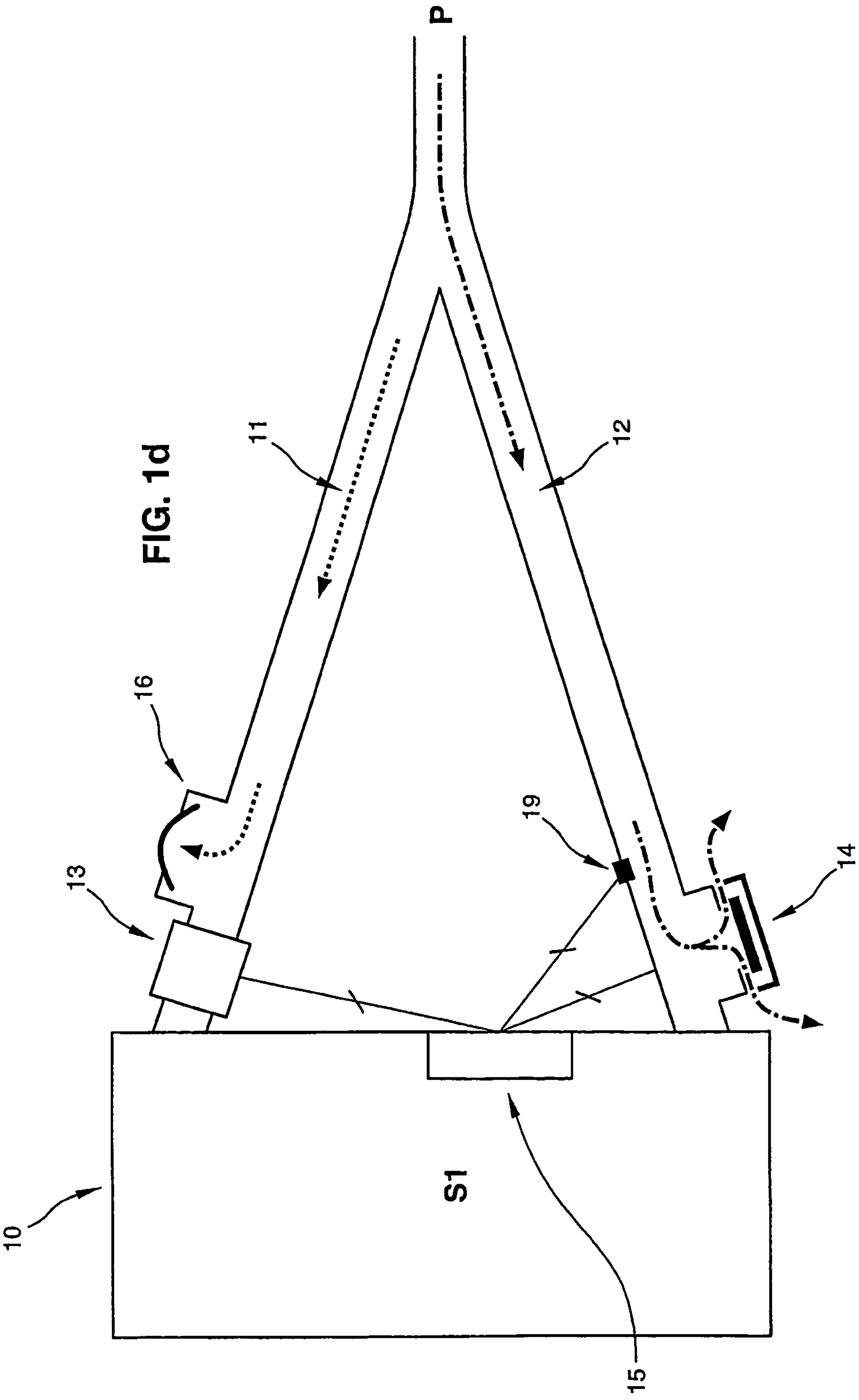
Figure 2A:
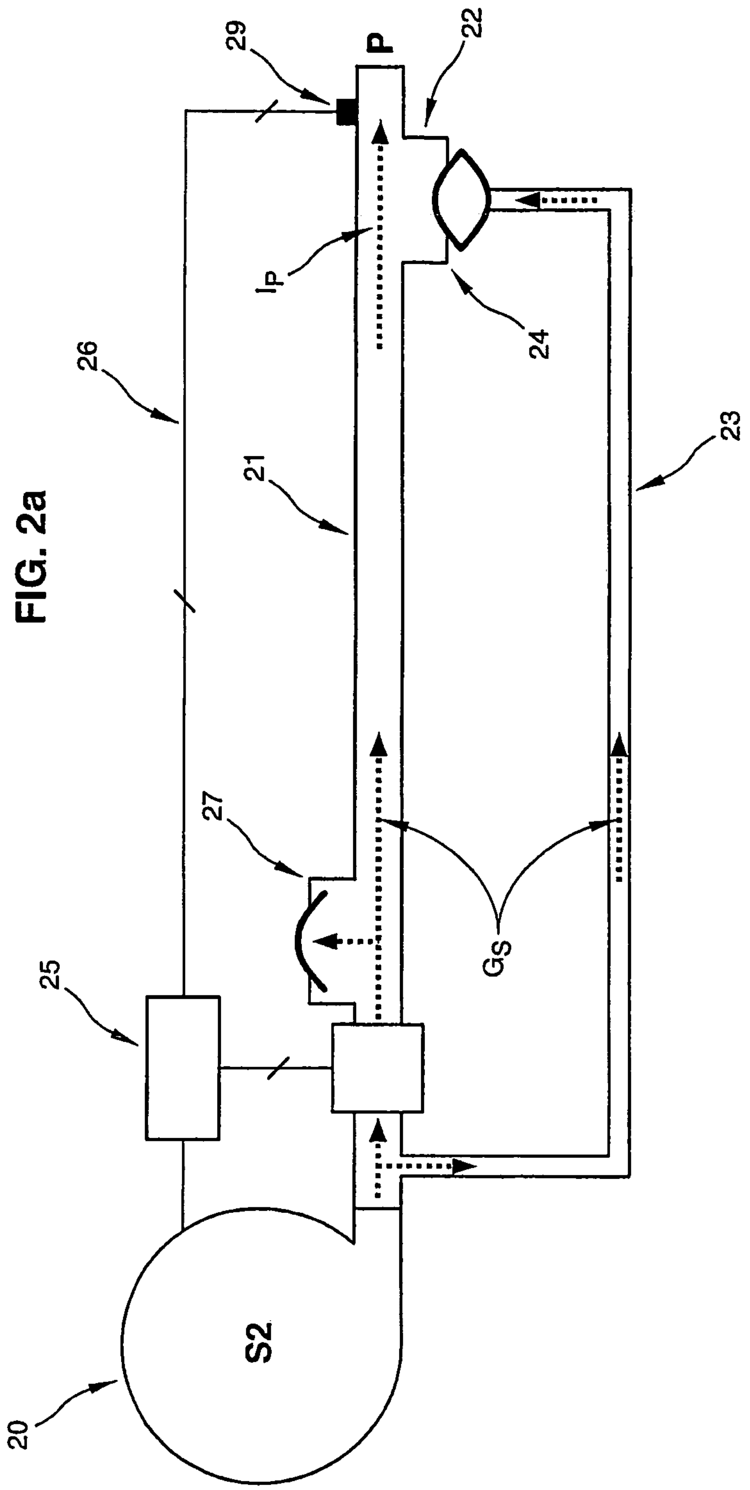
Figure 2B:
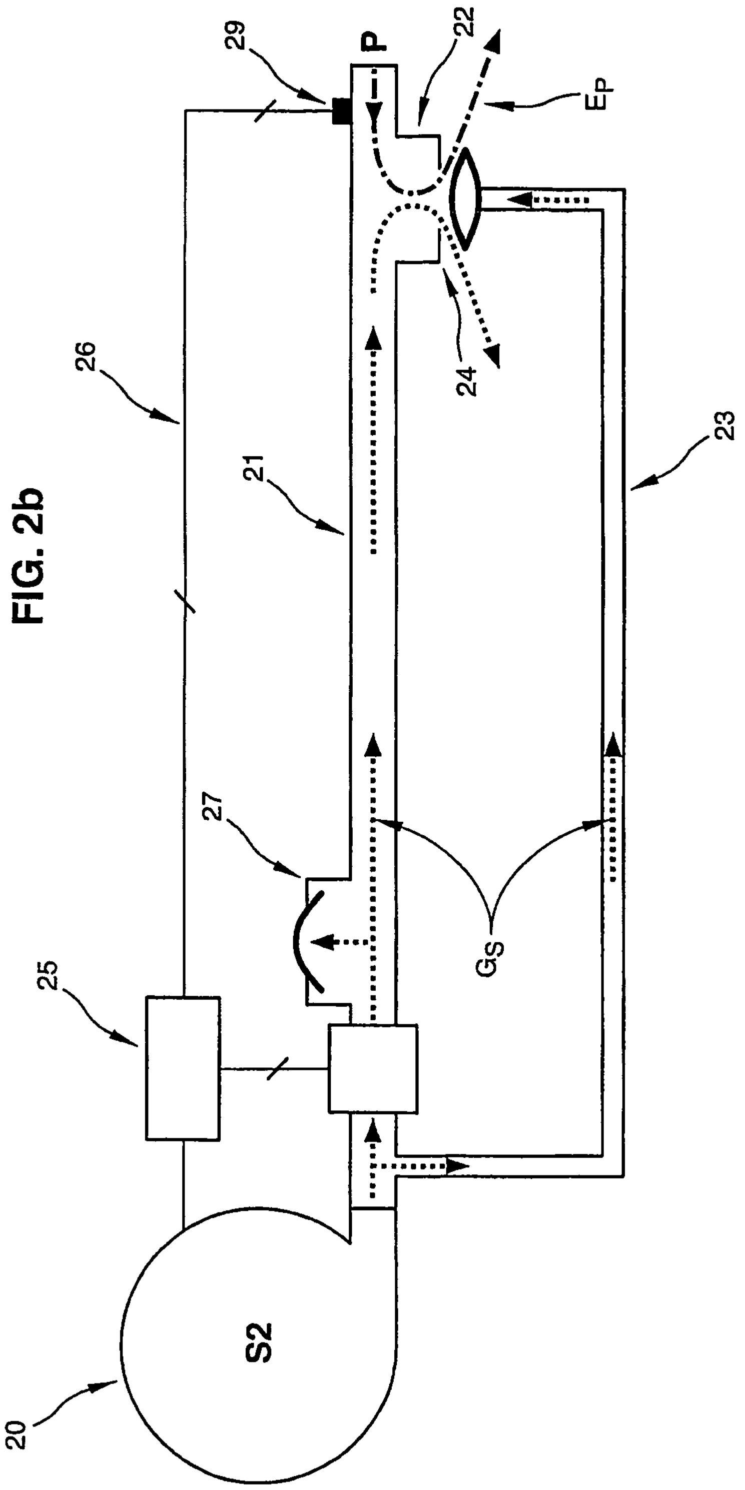
Figure 2C:
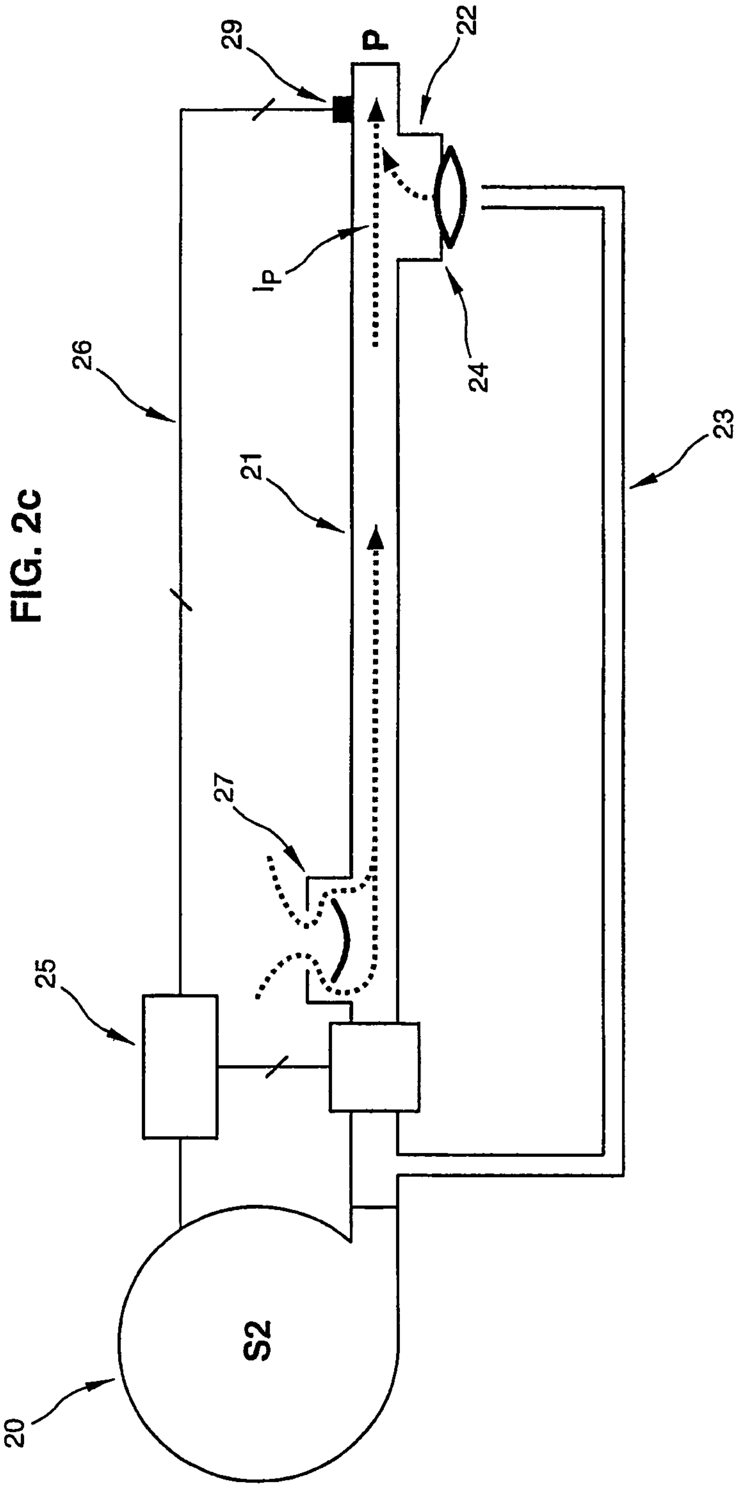
Figure 2D:
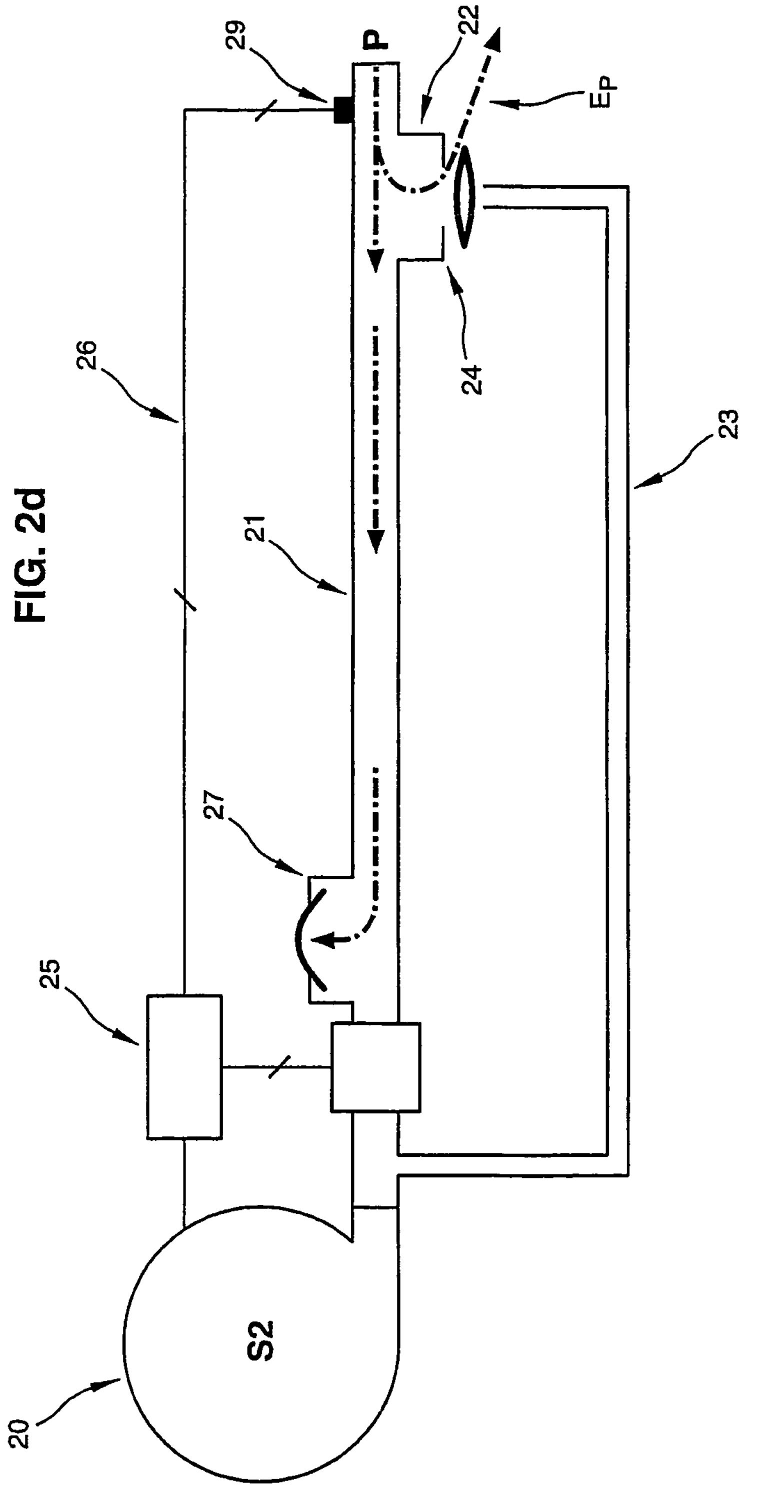
Figure 3:
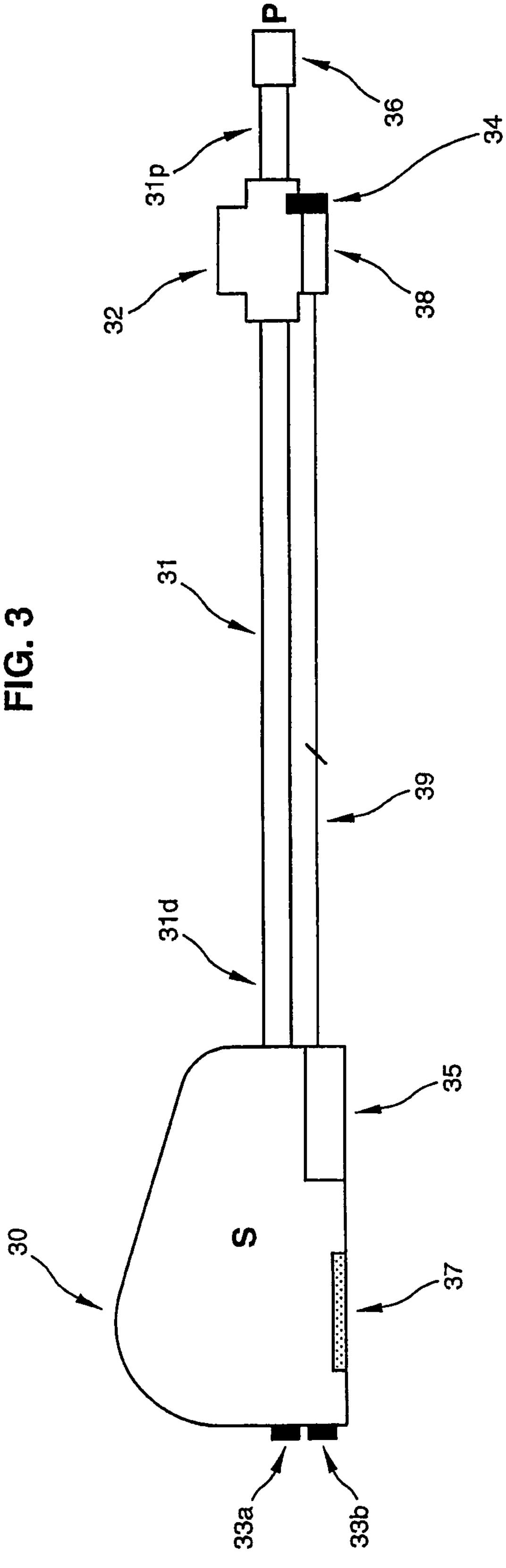
FIG. 3 is a schematic representation of a breathing assistance device according to the invention.

We shall first describe the general structure of a device (respirator) according to the invention. With reference to FIG. 3, a breathing assistance device according to the invention is shown in a schematic manner.

This device comprises a central unit 30, which itself includes an internal gas source S for feeding a patient P with respiratory pressurised gas. The gas source S is typically a small turbine.

The breathing assistance device further comprises a gas transmission circuit between the central unit 30 and the patient P, so as to allow the patient P to inspire and expire.

A gas regulating valve 32 is interposed in said gas transmission circuit at a proximal location. By proximal location, it has to be understood that the gas regulating valve 32 is located near the end of the gas transmission circuit coupled to the patient P.

The gas source S will preferably be capable of operating according to several respiratory modes.

This gas source is connected to an air inlet 33*a* for collecting ambient air to be provided to the patient P.

An additional inlet 33*b* may also be provided for a secondary respiratory gas such as oxygen, in order to enrich the ambient air.

The gas source S is powered through a power supply means 37. This power supply 37 means may be an internal battery or an external power supply.

The gas transmission circuit may be composed of one or more gas transmission ducts. As shown in FIG. 3, the breathing assistance device of the invention preferably includes a gas transmission circuit consisting of a single gas transmission duct 31.

This gas transmission duct 31 comprises a distal end 31*d* coupled to the source S and a proximal end 31*p* coupled to the patient P.

The proximal end 31*p* of the transmission duct 31 is connected to the patient P through a connecting means 36. This connecting means 36 may be e.g. a device adapted for tracheotomy or a mask.

The breathing assistance device further includes a controlling means 35 for controlling the gas regulating valve 32 via a connection link 39 (for data transmission and power supply). This connection link 39 can be a connection cable 39.

The controlling means 35 are associated to measurement means 34 (in particular a gas flow sensor and a pressure sensor).

More precisely, "associated to" means that the controlling means 35 either include such measurement means 34, or are connected to them via a connection link.

Part or all of these measurement means can indeed be located proximally, that is located near the gas regulating valve 32. It is also possible that part or all of these measurement means are located on the rest of the gas transmission duct 31, such as near its distal end 31*d*.

The controlling means 35 further includes data processing means, in particular to enable processing of the signals coming from the different measurement means.

The data processing means of the controlling means 35 are generally all located at a distal position, that is on the gas source S.

However, a data processing means 38 may be located at a proximal position, that is near the patient P. Indeed, the more measurement means there will be near the gas regulating valve 32, the more wires there will have to be in the connection cable 39 along the gas transmission duct 31, in order to power supply these measurement means but also to collect the different emitted signals.

It is therefore interesting to provide a proximal data processing means 38 so that the different signals from the measurement means can be processed to be transmitted to distal data processing means of the controlling means 35 through a single data transmission wire. Such a configuration of the data processing means will therefore emphasize the miniaturization process, the connection cable 39 between the distal data processing device and the proximal measurement means needing only three wires, i.e. one data transmission wire and two power supply wires.

The gas transmission duct 31 may be of different diameters. In particular, this gas transmission duct 31 may have a smaller diameter than the ducts used in the known breathing assistance devices as those represented in FIGS. 1*a* through 1*d* and 2*a* through 2*d.*

The particular gas regulating valve 32 of the invention, interposed in the gas transmission duct 31, enables namely to fulfil the pressure loss and security standards without needing a minimal diameter duct. It is therefore possible for the gas transmission duct 31 to have a diameter smaller than 22 mm for adults and 15 mm for children.

The gas regulating valve 32 has indeed a structure that emphasizes the miniaturization of the breathing assistance device. As exposed further in this text, the latter remains also highly secured and reliable.

First Embodiment of the Invention

The breathing assistance device according to a first embodiment of the invention comprises a gas regulating valve as represented in FIGS. 4*a* to 4*e*. The gas regulating valve 40 according to this embodiment of the invention is mounted coaxially relative to the gas transmission duct 31.

The gas regulating valve 40 includes a casing made of three hollow portions, namely a distal portion 41, a central portion 42 and a proximal portion 43.

The three portions are coaxially connected together so as to form an integral casing. Each portion is formed so that the casing comprises a passage through which the pressurised gas can circulate form the gas source S to the patient P and vice-versa.

The distal portion 41 and proximal portion 43 are formed to be connected to the gas transmission duct 31, respectively in direction of the source S and the patient P.

The distal portion 43 is provided with an aperture 431 so as to form a leakage orifice between the inside and the outside of the gas regulating valve 40. Gas may therefore leak from the gas transmission circuit to the atmosphere and vice-versa. It is preferred that this aperture is as wide as possible, that is the aperture covers most of the circumference of the distal portion 43.

The gas regulating valve 40 further includes an obstruction means 44 in order to vary the opening of the leakage orifice. The obstruction means 44 is preferably an electromagnetic obstruction means.

The obstruction means 44 includes a metallic toric sheath 441, preferably made of soft iron, wherein a coil 442 is fixed. This assembly is fixed around the proximal portion 43 and is surrounded by the central portion 42 of the casing.

The coil 442 may be a single toric coil but it is preferable to use two coaxial toric coils, both surrounded by the toric sheath 441. The coil 442 is powered by the controlling means 35 via the connection cable 39.

The obstruction means 44 further includes a magnetic element comprising a toric magnet 444, a first polar piece 443 and a second polar piece 445. The polar pieces are coaxially fixed on either side of the toric magnet 444, and are of different polarities. The polar pieces have a rotational symmetry relative to the axis of revolution of the toric magnet 444 and include a passage through which gas can circulate from the source S to the patient P and vice-versa.

This magnetic element is arranged within the proximal portion 43 and is at least partially surrounded by the coil 442. The magnetic element is movable within the proximal portion 43, it is namely translatable along the axis of revolution of the toric magnet 444. This translation movement is at least partially confined within the coil 442, the two extreme positions being defined by abutments provided in the inner side of the casing.

The magnetic element is provided with an obstruction piece 446 capable of obstructing the leakage orifice 431 of the proximal portion 43. This obstruction piece 446 is fixed on a polar piece of the magnetic element and follows therefore the translation movement of the magnetic element.

Dimension and shape of the obstruction piece 446 depend on the characteristics of the leakage orifice 431 and the magnetic element. The obstruction means 44 must namely be dimensioned so that the obstruction piece 446 totally closes the leakage orifice 431 when the magnetic element is positioned in one of its two extreme positions. The obstruction piece 446 is also preferably made of a hard material.

The magnetic element is therefore composed of different pieces, whose shapes and assemblage allow a passage, through which gas can circulate form the gas source S to the patient P and vice-versa.

Another arrangement of this embodiment of the invention would be to have an obstruction means including a fixed magnetic element, that is at least a fixed magnet, and a movable coil, said movable coil being provided with an obstruction piece so as to be capable of obstructing the leakage orifice of the proximal portion.

Second Embodiment of the Invention

Another embodiment of a breathing assistance device according to the invention comprises a gas regulating valve as represented in FIGS. 5*a* to 5*e*. The gas regulating valve 50 of this second embodiment is very similar to the gas regulating valve 40 according to a first embodiment of the invention.

The gas regulating valve 50 of the second embodiment has namely the same structure as the gas regulating valve 40 according to a first embodiment of the invention, in particular concerning the obstruction means. However, the gas regulating valve 50 comprises a proximal portion 53 being provided with a housing 532 for measurement means connected to the controlling means 35 via the connection cable 39.

There is for example provided a gas flow pressure sensor (such as a hot wire sensor) and a pressure sensor. In this case the connection cable 39 comprises at least seven wires. There will namely be needed two power supply wires for the flow pressure sensor, two power supply wires and a data transmission wire for the pressure sensor, and two additional wires to power supply the magnetic mechanism of the gas regulating valve 50.

Third Embodiment of the Invention

A third embodiment of a breathing assistance device according to the invention comprises a gas regulating valve as represented in FIGS. 6*a* to 6*e*. The gas regulating valve 60 according to this embodiment of the invention is mounted transversally relative to the gas transmission duct 31.

The gas regulating valve 60 comprises a casing 61 having a distal end 611 and a proximal end 612, the distal end 611 being coupled to the gas transmission duct 31 in direction of the source S and the proximal end 612 being coupled to the gas transmission duct 31 in direction of the patient P.

The casing 61 has a shape very similar to a duct except the fact that it also includes a housing 613 for receiving an obstruction means 62.

A first aperture 614 is provided between the duct 616 of the casing 61 and a first zone 6131 of the housing 613.

A second aperture 615 is provided in the first zone 6131 of the housing 613, so that a gas flow may circulate between the inside of the casing 61 and the outside.

The first and second apertures (614,615) thus define a leakage orifice 617. Gas may circulate through this leakage orifice 617 from the gas transmission circuit to the atmosphere and vice-versa A cover 63 is foreseen to close the housing 613 and protect the obstruction means 62 disposed in a second zone 6132 of said housing 613.

The obstruction means 62 is preferably an electromagnetic obstruction means.

The obstruction means 62 comprises a metallic armature 622 which is fixed in the second zone 6132 of the housing 613. This armature 622 may be made of soft iron. The armature 622 comprises a cylindrical passage 6221 whose axis of revolution is perpendicular to the duct 616 of the casing 61.

The armature 622 is preferably a revolution solid whose axis of revolution corresponds to the axis of revolution of the cylindrical passage 6221. The armature 622 comprises a bottom disc 6222 having a circular opening at its centre and a top disc 6223 having a circular opening at its centre, the diameters of the bottom disc 6222 and of the circular opening of the bottom disc 6222 being respectively larger than the diameters of the top disc 6223 and of the circular opening of the top disc 6223.

Bottom and top discs (6222,6223) are coaxially coupled together through a peripheral coaxial cylindrical portion 6224 having the same diameter as the one of the bottom disc's circular opening.

A central coaxial cylindrical portion 6225 is provided in the armature 622, between the bottom disc 6222 and the top disc 6223. This central coaxial cylindrical portion 6225 has the same diameter as the one of the top disc's circular opening, and has an end fixed to the top disc 6223.

A central disc 6226 having the same diameter as the one of the central coaxial cylindrical portion 6225 is coaxially fixed to the other end of the central coaxial cylindrical portion 6225. This central disc 6226 is provided with a circular opening at its centre.

In this configuration, the peripheral and central coaxial cylindrical portions (6224, 6225) of the armature 622 define a toric space 6227.

The obstruction means 62 further comprises a coil 621 that surrounds the first cylindrical portion of the armature 622.

This configuration creates therefore an air-gap in the toric space 6227, between the coil 621 and the central coaxial cylindrical portion 6225 of the metallic armature 622, which is closed at one end with the top disc 6223 of the armature 622.

The obstruction means 62 also includes a magnetic element, the magnetic element comprising a toric magnet 624 and a magnet guide 623.

The magnet guide 623 is a revolution solid comprising a bottom disc 6231 and a top disc 6232 of a larger diameter, the top disc 6232 having a circular opening at its centre, the diameter of this opening being the same as the diameter of the top disc. The bottom and top discs (6231,6232) are coaxially coupled through a peripheral coaxial cylindrical portion 6233 having a diameter identical to the diameter of the bottom disc 6231. A central coaxial cylindrical portion 6234 having a smaller diameter is provided on the bottom disc 6231, between the top and bottom discs (6232,6231).

The toric magnet 624 has an inner diameter similar to the diameter of the first cylindrical portion 6233 of the magnet guide 623, so that the magnet guide 623 is inserted within the toric magnet 624.

The outer diameter of the toric magnet 624 is similar to the inner diameter of the peripheral coaxial cylindrical portion 6224 of the armature 622. The diameter of the circular opening of the top disc 6232 of the magnet guide 623 is similar to the outer diameter of the central coaxial cylindrical portion 6225 of the armature 622. The central coaxial cylindrical portion 6234 of the magnet guide 623 has an outer diameter similar to the diameter of the circular opening of the central disc 6226 of the armature 622. Therefore the magnetic element can be coaxially inserted within the toric space 6227 defined by the peripheral and central coaxial cylindrical portions (6224,6225) of the armature 622.

The magnetic element is movable, it is namely translatable along the axis of revolution of the armature 622, within the toric space 6227 defined by the peripheral and central coaxial cylindrical portions (6224,6225) of the armature 622.

An annular ridge 6228 is provided within the housing 613 on the periphery of the first aperture 614. The outer diameter of the toric magnet 624 is larger than the diameter of the first aperture 614. Therefore the translation movement of the magnetic element is confined between the armature 622 and the first aperture 614. More precisely the magnetic element abuts against the armature 622 in a first extreme position and against the annular ridge 6228 of the first aperture 614 in a second extreme position.

In the second extreme position, the magnetic element of the obstruction means 62 totally closes the first aperture 614 and thus prevents any gas flow between the duct 616 of the gas regulating valve 60 and the housing 613. As a consequence, in this second extreme position, no gas can circulate between the inside and the outside of the gas regulating valve 60.

In this configuration of the obstruction means 62, the magnetic element translates within the toric space 6227 depending on the state of the coils 621 controlled by the controlling means 35.

The obstruction means 62 further comprises a spring 626 having an outer diameter similar to the inner diameter of the central coaxial cylindrical portion 6225 of the armature 622, and which is inserted within said central coaxial cylindrical portion 6225 of the armature 622. The spring 626 is preferably a compression spring.

The spring 626 is maintained within the central coaxial cylindrical portion 6225 of the armature 622 with a screw 627 which is screwed within the central coaxial cylindrical portion 6225 of the magnet guide 623. The spring 626 has namely an end abutting against the head of the screw 627 and another end abutting against the central disc 6226 of the armature 622

The gas regulating valve 60 may comprise a protection element 625 within the housing 613 of the casing 61. This protection element 625 delimits the first and second zones within the housing 613, the first zone 6131 wherein the first and second apertures (614,615) are located and the second zone 6132 containing the obstruction means 62.

The protection element 625 is gas permeable and prevents therefore gas within the duct of the gas regulating valve 62 from polluting the obstruction means 62.

The protection element 625 may be a rubber membrane. This membrane is a revolution solid comprising a central disc 6251, this central disc 6251 having a relatively large peripheral and circular groove 6252.

The peripheral edge of the protection element 625 is pressed by the armature 622 against a circular abutment between the first and the second zone of the housing 613. The annular ridge 6228 of the armature 622 prevents the peripheral edge of the protection means 625 from moving.

Another arrangement of this embodiment of the invention resides in an obstruction means comprising a magnetic element being fixed, that is at least a magnet being fixed, and a movable coil, said movable coil allowing the obstruction of the leakage orifice.

The housing 613 may comprise a third zone 6133 for receiving measurement means 65 such as gas flow and/or pressure sensors for measuring gas flow and/or pressure in the duct of the gas regulating valve 60.

The measurement means 65 may be directly connected to the controlling means 35 located on the source S, via the connection cable 26. In this case, the connection cable 39 is provided with a least seven wires (two power supply wires for the flow pressure sensor, two power supply wires and a data transmission wire for the pressure sensor, and two additional wires to power supply the magnetic mechanism of the gas regulating valve).

Therefore, a processing means 64 is preferably provided between the measurement means 65 and the connection cable 39. This processing means 64 is located within the housing 613 and lies on both the measurement means 65 and the obstruction means 62.

The processing means 64 is connected to both the measurement means 65 and the obstruction means 62. Thus the processing means 64 allows the measurement means 65 and the obstruction means 62 to be power supplied. Moreover the processing means 64 is capable of managing the data from the measurement means 65 in order to precisely control the obstruction means 62. The processing means 64 is capable of controlling the PEP, in processing the data from the measurement means 65 and operating the obstruction means 62 in consequence.

The connection cable 39 between the processing means 64 and the controlling means 35 is also much simpler, being provided only with three wires, i.e. two power supply wires and one data wire.

The control of the gas regulating valve 60 being totally operated by the processing means 64, the controlling means 35 located in the central unit 30 may also be simplified, if not totally removed. This thus contributes to the miniaturization of the breathing assistance device.

Operation of the Device

The breathing assistance device according to the invention is capable of being operated even if the gas source S and/or the controlling means 35 are disabled (e.g. in case of a breakdown).

We shall describe the operation of the breathing assistance device in different cases, as illustrated in FIGS. 7*a* to 7*c* and FIGS. 8*a* to 8*b*.

Normal Operation

The normal operation of the device corresponds to the case when both the gas sources S and the controlling means 35 operate normally.

Figures 7A, 7B, 7C:
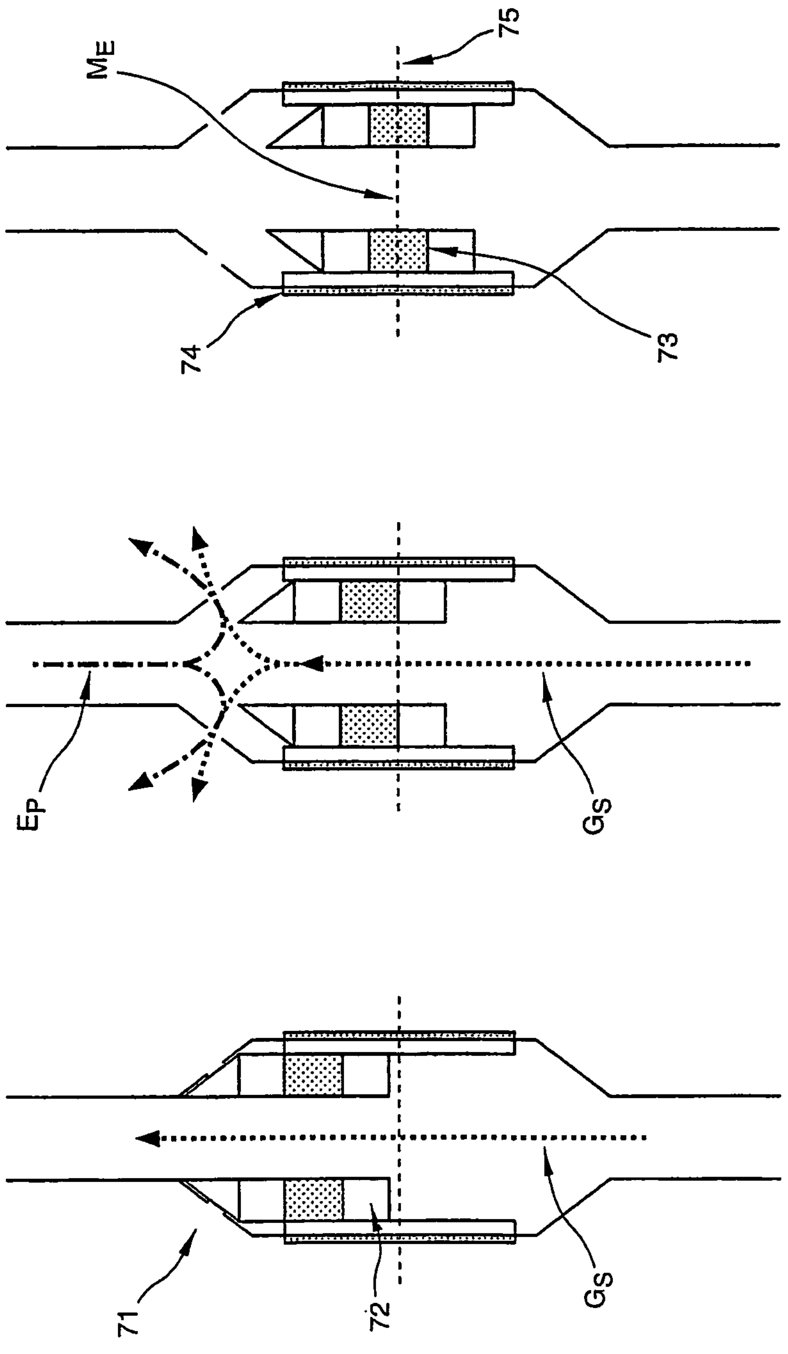
FIG. 7*a* is a schematic representation of a gas regulating valve according to the first and second embodiments of the invention, in normal operation, during the inspiration phase.
FIG. 7*b* is a schematic representation of a gas regulating valve according to the first and second embodiments of the invention, in normal operation, during the expiration phase.
FIG. 7*c* is a schematic representation of a gas regulating valve according to the first and second embodiments of the invention, when the controlling means is disabled.
Figure 8A:
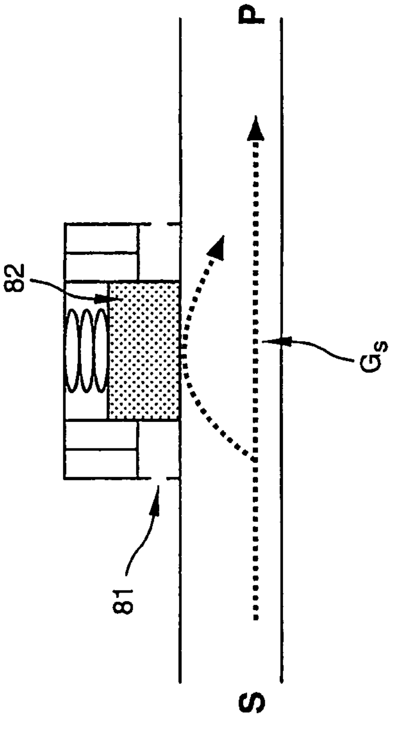
FIG. 8*a* is a schematic representation of a gas regulating valve according to the third embodiment of the invention, in normal operation, during the inspiration phase.

During the inspiration phase, the obstruction means (72;82) of the gas regulating valve is an extreme position so that the leakage orifice (71;81) of the gas regulating valve is totally obstructed, as illustrated in FIGS. 7*a* and 8*a*.

As a consequence, when the patient P inspires, the pressurised gas $G_S$ coming from the gas source S is transmitted to the patient P. The leakage orifice (71;81) of the gas regulating valve being namely closed, the pressurised gas $G_S$ can circulate in the gas transmission duct until the patient P.

Figure 4A:
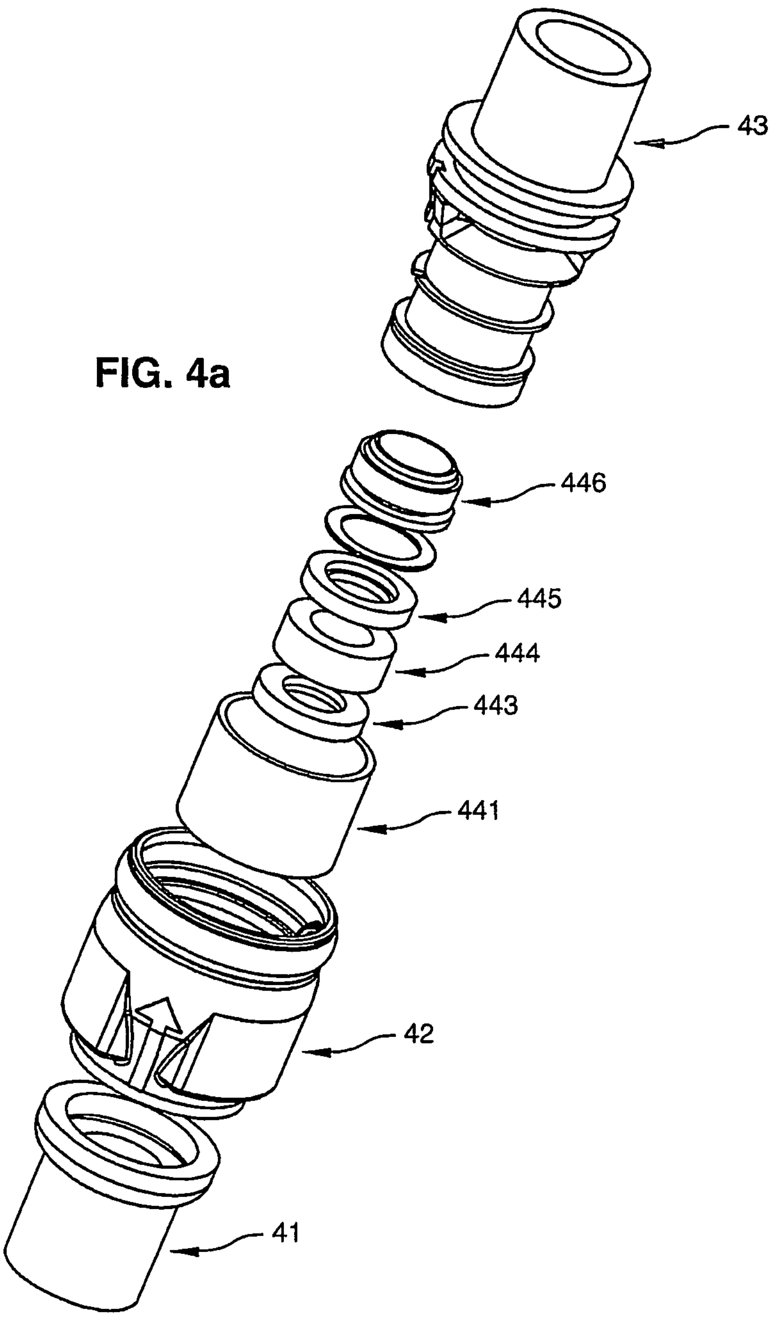
FIG. 4*a* is a three-dimensional exploded view of a gas regulating valve according to a first embodiment of the invention.
Figure 4B:
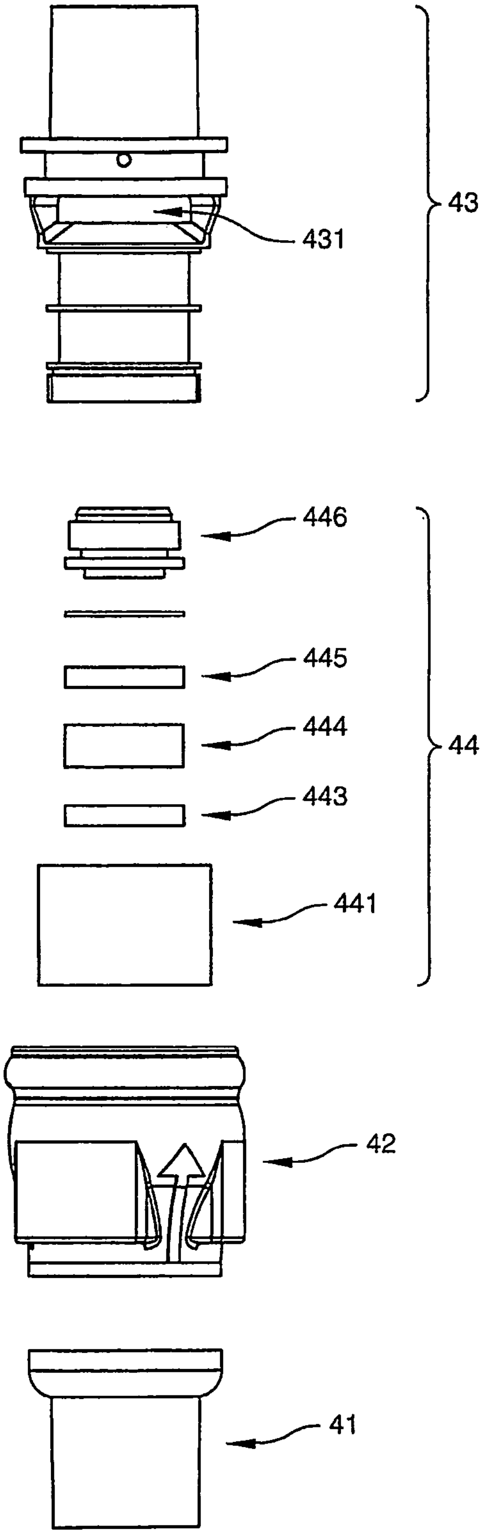
FIG. 4*b* is a plan exploded view of the gas regulating valve of FIG. 4*a;*
Figure 4D:
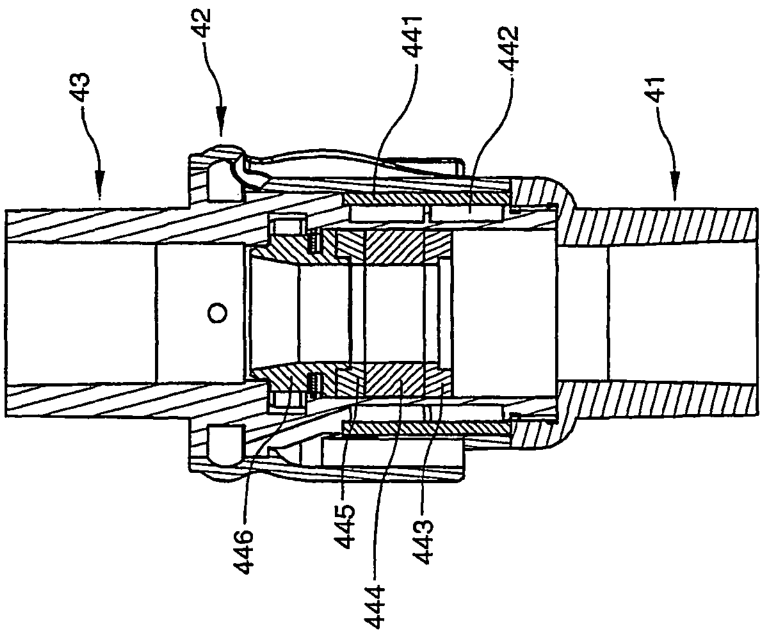
FIG. 4*d* is a sectional view of the gas regulating valve of FIG. 4*a* with a closed leakage orifice.
Figure 4C:
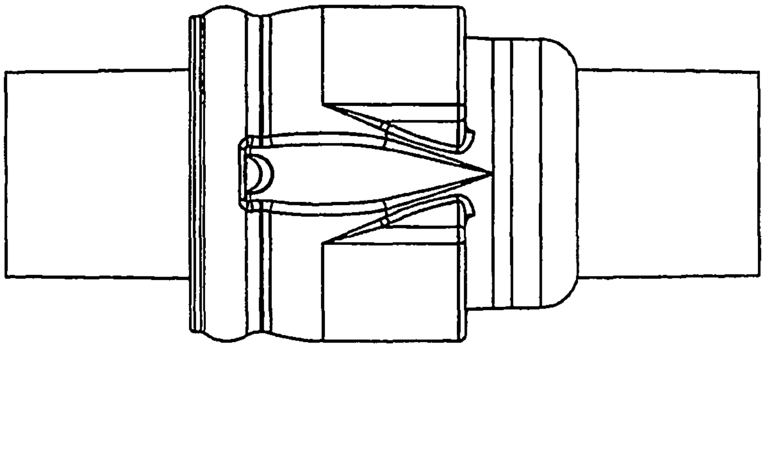
FIG. 4*c* is a side view of the gas regulating valve of FIG. 4*a;*
Figure 5A:
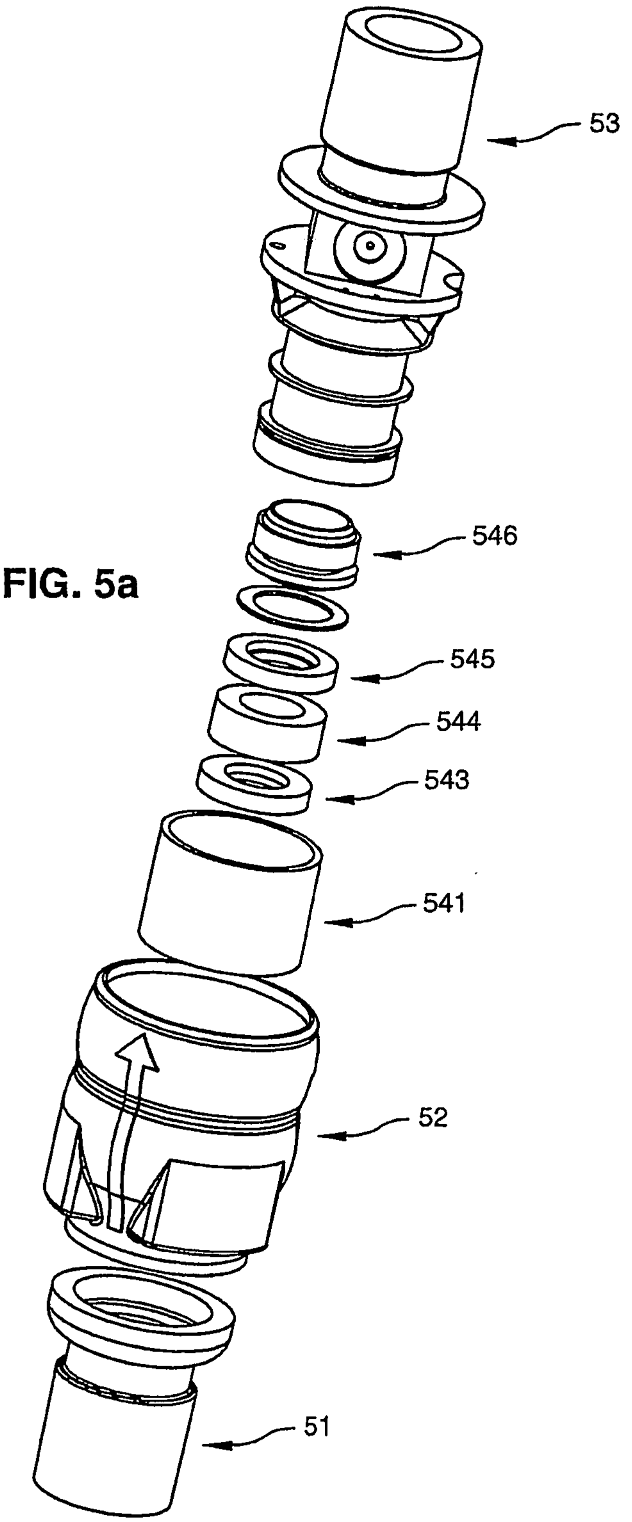
FIG. 5*a* is a three-dimensional exploded view of a gas regulating valve according to a second embodiment of the invention.
Figure 5B:
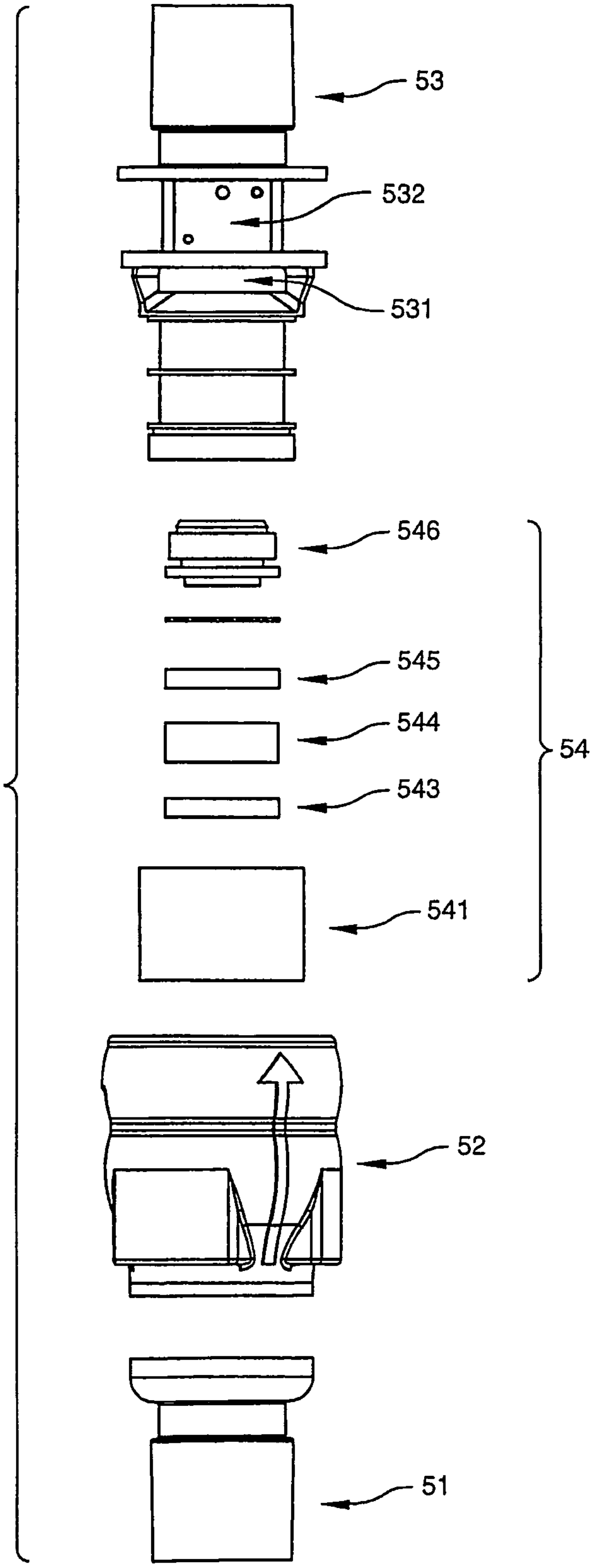
FIG. 5*b* is a plan exploded view of the gas regulating valve of FIG. 5*a;*
Figure 5D:
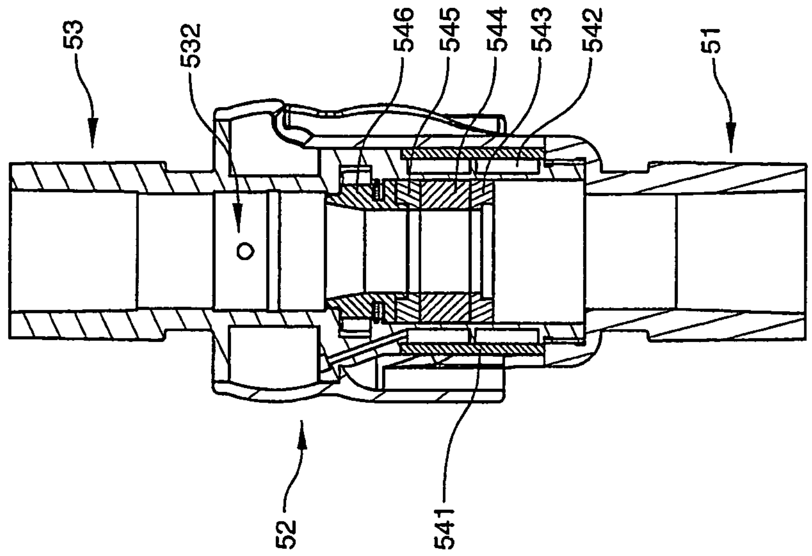
FIG. 5*d* is a sectional view of the gas regulating valve of FIG. 5*a* with a closed leakage orifice.
Figure 5C:
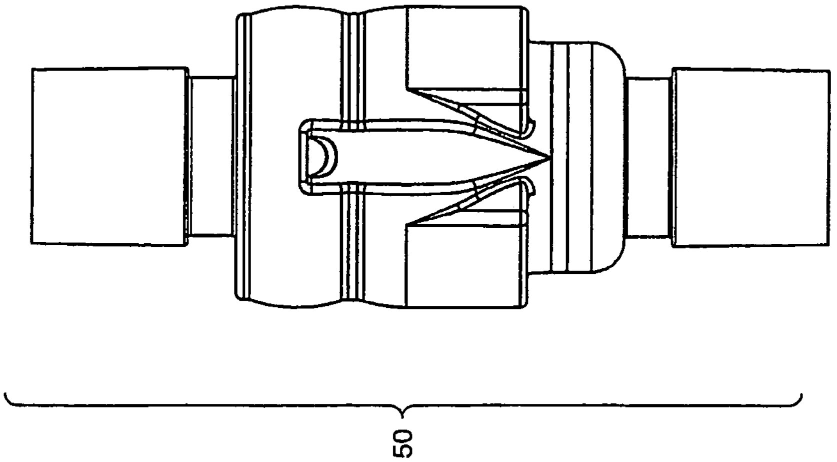
FIG. 5*c* is a side view of the gas regulating valve of FIG. 5*a;*

FIGS. 4*d* and 5*d* represent the gas regulating valve (40;50) according to the first and second embodiments of the invention during the inspiration phase, that is when the leakage orifice (431;531) is totally closed.

In this case, the controlling means 35 operates the coil (442;542) of the obstruction means (44;54) so that the magnetic element translates within the proximal portion (43;53) of the gas regulating valve (40;50) and abuts against an abutment provided within the proximal portion (43;53) of the gas regulating valve (40;50).

Therefore the obstruction piece (446;546) of the magnetic element totally closes the leakage orifice (431;531). The passage between the inside and the outside of a gas regulating valve (40;50) is thus closed and the pressurised gas coming from the gas source S only circulates from the distal portion (41;51) to the proximal portion (43;53) and then to the patient P.

Figure 6A:
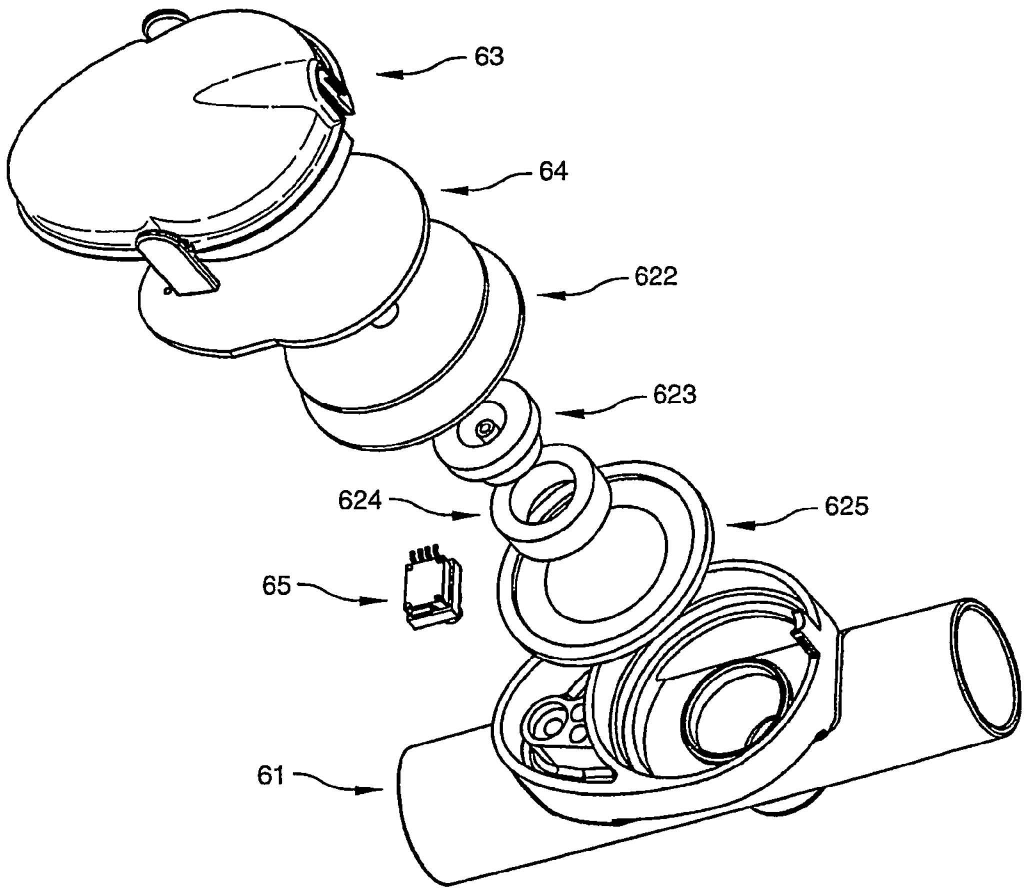
FIG. 6*a* is a three-dimensional exploded view of a gas regulating valve according to a third embodiment of the invention.
Figure 6B:
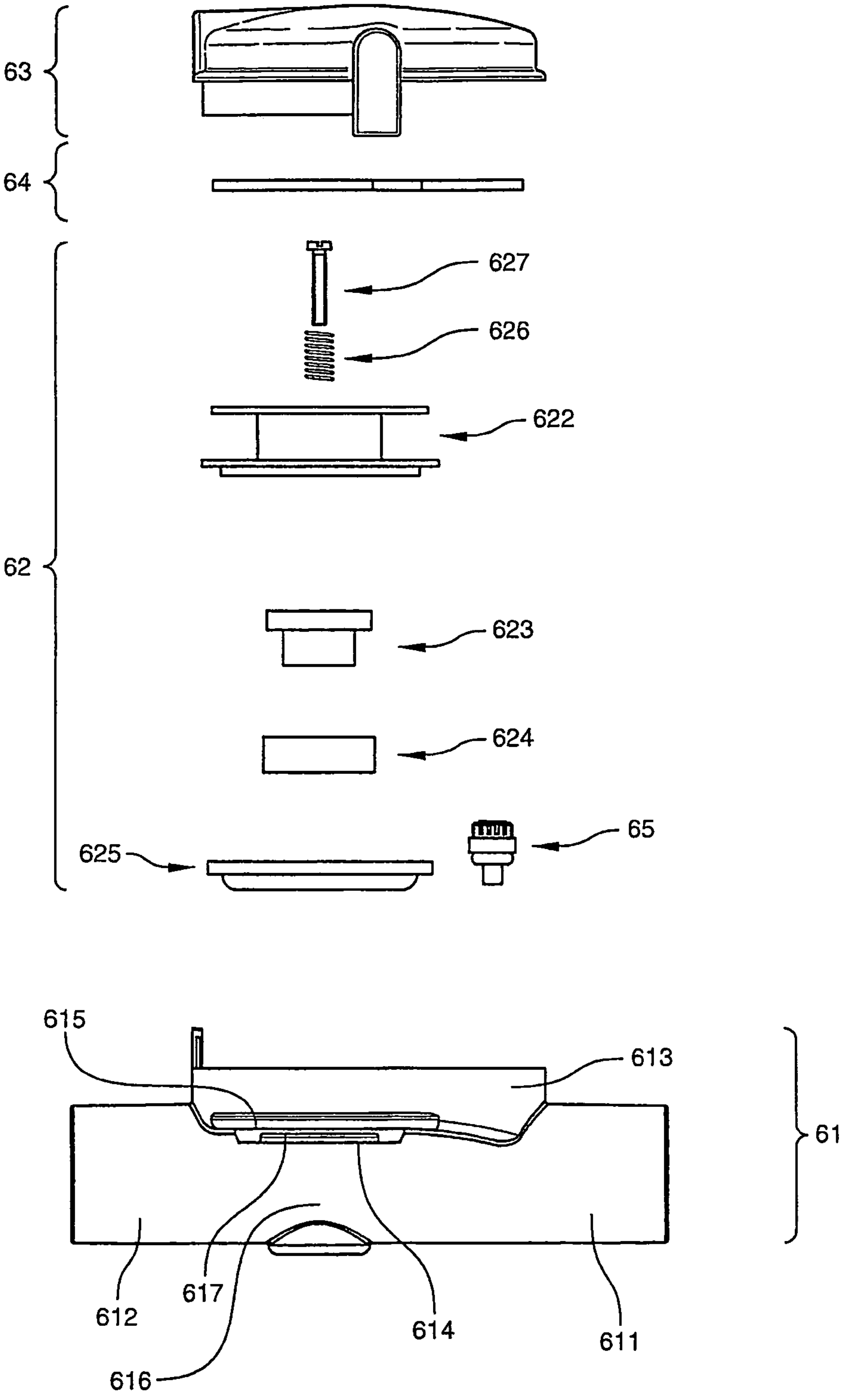
FIG. 6*b* is a exploded plan view of the gas regulating valve of FIG. 6*a;*
Figure 6E:
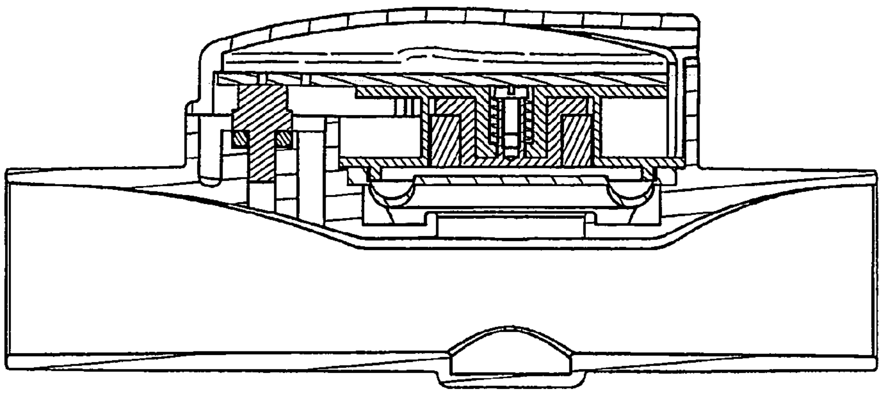
FIG. 6*e* is a sectional view of the gas regulating valve of FIG. 6*a* with an opened leakage orifice.
Figure 6C:
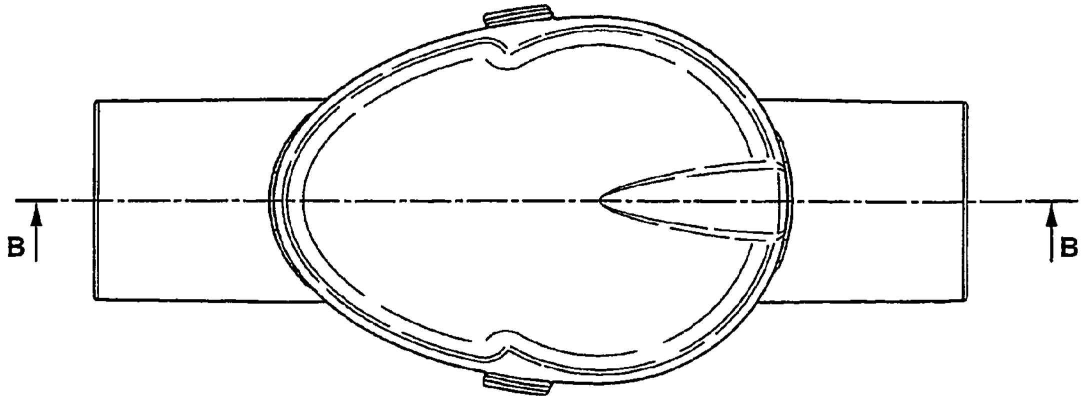
FIG. 6*c* is a side view of the gas regulating valve of FIG. 6*a;*
Figure 6D:
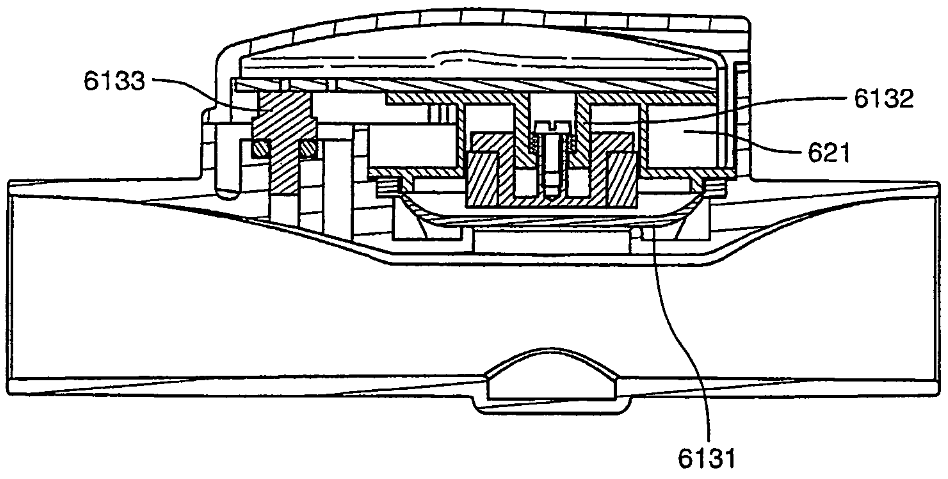
FIG. 6*d* is a sectional view of the gas regulating valve of FIG. 6*a* with a closed leakage orifice.
Figure 6F:
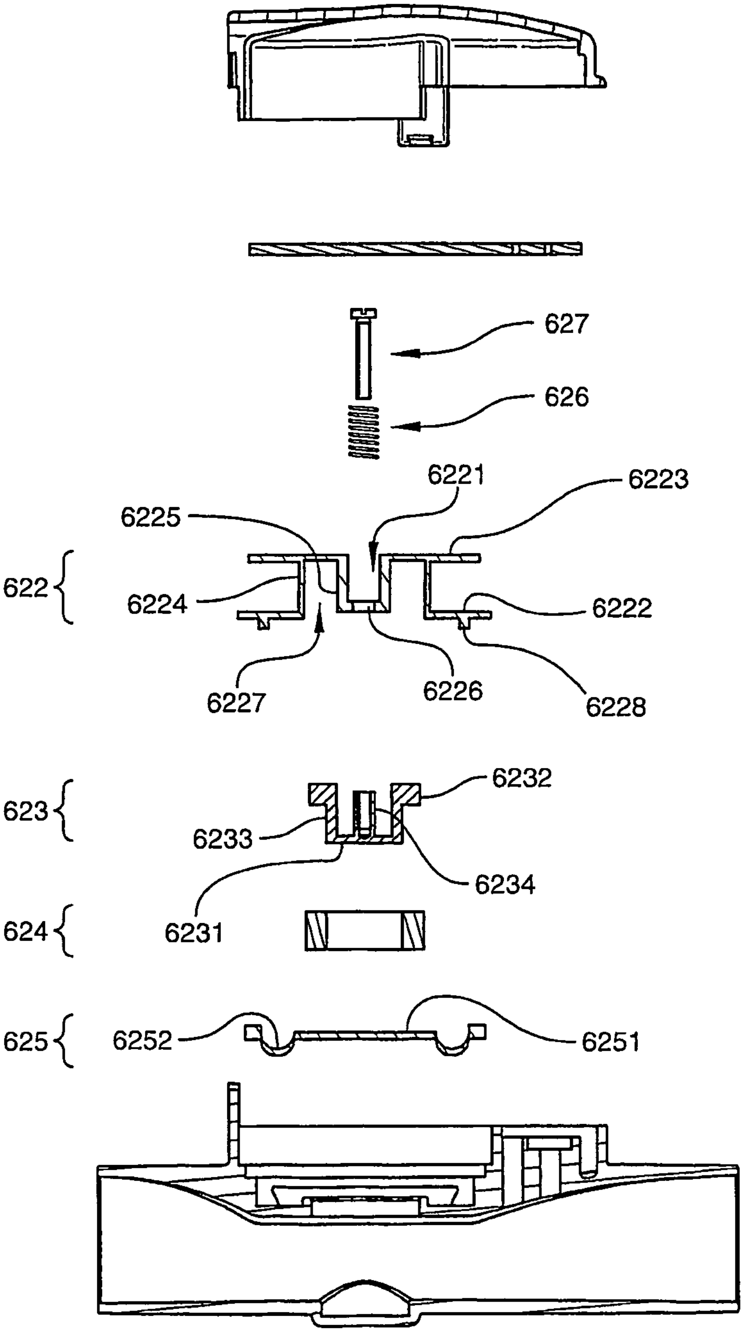
FIG. 6*f* is an exploded sectional view of the gas regulating valve of FIG. 6*a;*

FIG. 6*d* illustrates the gas regulating valve 60 according to the third embodiment of the invention during the inspiration phase, that is when the leakage orifice 617 is totally closed.

In this case the controlling means 35 operates the coil 621 of the obstruction means 62 so that the magnetic element translates until it abuts against the annular ridge 6228 of the housing 613.

Therefore the leakage orifice 617 is closed and no gas can circulate between the inside and the outside of the gas regulating valve 60. The magnetic element namely obstructs the passage provided through the first aperture 614 of the housing 613. In this situation, the pressurised gas $G_S$ coming from the gas source S has no other way but to reach the patient P.

Figure 8B:
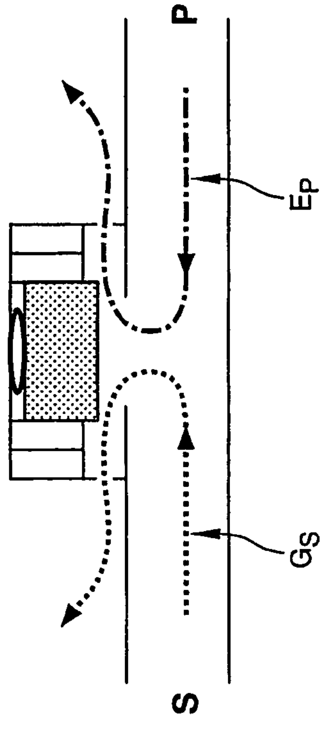
FIG. 8*b* is a schematic representation of a gas regulating valve according to the third embodiment of the invention, in normal operation, during the expiration phase.

During the expiration phase as illustrated in FIGS. 7*b* and 8*b*, the leakage orifice (71;81) is at least partially opened. The obstruction means (72;82) has namely a position so that the gas flow can circulate between the inside and the outside of the gas regulating valve through the leakage orifice (71;81).

In this case, the patient P rejects expiratory gases $E_P$ that have to be evacuated. The leakage orifice (71;81) of the gas regulating valve allows such an evacuation of the expiratory gases.

Controlling the opening of the leakage orifice (71;81) with the obstruction means (72;82) of the gas regulating valve is also a way of controlling the PEP. The PEP in the gas transmission duct is namely important for the patient P to expire correctly, as the PEP is a way to balance the residual overpressure in the patient lungs.

The obstruction means being electrically controlled, the control of the opening of the leakage orifice is a real time process.

Figure 4E:
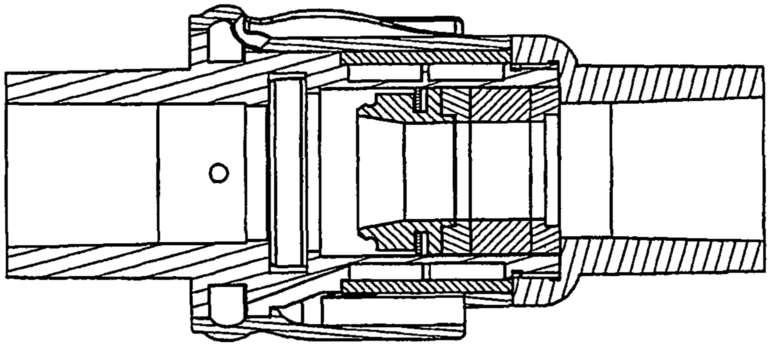
FIG. 4*e* is a sectional view of the gas regulating valve of FIG. 4*a* with an opened leakage orifice.
Figure 5E:
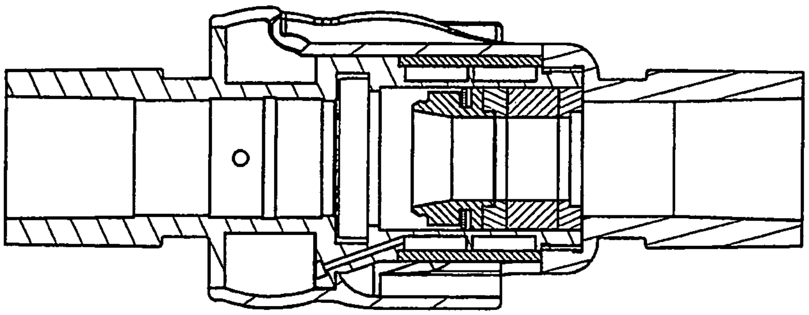
FIG. 5*e* is a sectional view of the gas regulating valve of FIG. 5*a* with an opened leakage orifice.

FIGS. 4*e* and 5*e* illustrate the gas expiratory valve (40;50) according to the first and second embodiments of the invention, during the expiration phase.

These figures namely show gas regulating valves having a leakage orifice (431;531) totally opened. The obstruction means (44;54) has indeed been operated by the controlling means 35 through the coil (442;542) so as to translate until an abutment provided on the distal portion (41;51) of the gas regulating valve (40;50).

FIG. 6*e* illustrates a gas regulating valve 60 according to the third embodiment of the invention during the expiration phase.

This figure namely shows a leakage orifice being totally opened. In fact, the magnetic element of the obstruction means 62 has been operated by the controlling means 35 through the coil 621 in order to translate until abutting against the armature 622.

In this position, the first aperture 614 between the duct 616 and the housing 613 of the gas regulating valve is wildly opened. A gas flow can therefore circulate between the duct 616 of the gas regulating valve 60 and the housing 613, this gas flow being then able to circulate from the first zone of the housing 613 to the outside of the gas regulating valve 60 through the leakage orifice 617.

It is to be noticed that the opening of the first aperture 614 between the duct 616 and the housing 613 of the gas regulating valve 60 can be precisely controlled in translating the magnetic element of the obstruction means 62.

Operation of the Device when the Gas Source is Disabled

When the gas source S is disabled, e.g. when it breakdowns, the patient P must however be able to breathe. The gas regulating valve according to the invention allows the patient P to breathe normally in such a case.

The controlling means of the breathing assistance device will namely operate the gas regulating valve so that the leakage orifice reminds opened or at least partially opened during both inspiration and expiration phases.

During the expiration phase, the patient P will namely be able to expire through the gas regulating valve as in normal operation of the breathing assistance device.

Indeed, during expiration phases the pressurised gas, coming from the gas source, has only a role for controlling the PEP. However the controlling means allows a very precise and real time control of the opening of the leakage orifice through the control of the obstruction means. Therefore the absence of pressurised gas coming from the gas source can be counterbalanced in specifically operating the opening of the leakage orifice.

The inspiration phase is also possible as the leakage orifice of the gas regulating valve is opened and allows a gas flow between the inside and the outside of the gas regulating valve. Therefore the patient P will be able to inspire air from the atmosphere through the leakage orifice of the gas regulating valve.

Operation of the Device when the Controlling Means is Disabled

When the controlling means is disabled, e.g. when the controlling means breakdowns, the abstraction means cannot be controlled anymore. Therefore a return means is provided within the gas regulating valve so that the leakage orifice remains opened in the absence of signal from the controlling means.

The leakage orifice of the gas regulating valve remaining opened when the controlling means is disabled, the patient P can both inspire and expire through the leakage orifice of the gas regulating valve.

However, the opening of the leakage orifice being not controllable, it will not be possible to control the PEP anymore.

The gas regulating valve (40;50) of the first and second embodiments comprise a return means that consists in the metallic toric sheath (441,541) and the toric magnet (444, 544). The toric magnet (444,544) being coaxially disposed within the metallic toric sheath (441,541), this naturally defines a magnetic equator $M_E$.

Indeed, as illustrated in FIG. 7*c*, the toric magnet 73, in the absence of signal from the controlling means, remains located in the centre of the metallic toric sheath 74 because of the magnetic forces operating between the toric magnet 73 and the metallic toric sheath 74. The plan defined by the position of the toric magnet 73 is the magnetic equator $M_E$.

The obstruction means 72 of the gas regulating valve is preferably shaped so that the leakage orifice 71 is widely opened when the controlling means is disabled, that is when the toric magnet 73 of the obstruction means 72 is located on the magnetic equator $M_E$.

The gas regulating valve 60 of the third embodiment of the invention also comprises a return means. This return means comprises the spring 626 and the screw 627.

As illustrated in FIGS. 6*d* and 6*e*, the spring 626 is a compression spring. This compression spring 626 is compressed when the controlling means controls the coil 621 so that the magnetic element abuts against the circular ridge of the first aperture 614, that is when the leakage orifice is closed (as illustrated in FIG. 6*d*).

If the controlling means is disabled, the magnetic element will not be constraint by the coil 621 anymore and is therefore able to translate freely in the toric space 6227. The magnetic element being however coupled with the compression spring 626 via the magnet guide 623, the compression spring 626 draws the magnetic element against the top disc of the armature 622.

In case the controlling means is disabled, the compression spring 626 will translate the magnetic element of the obstruction means 62, having therefore a leakage orifice widely opened (as illustrated in FIG. 6*e*).

Operation of the Device when Both the Gas Source and the Controlling Means are Disabled In this case, the patient P will be able to breathe thanks to the return means provided in the gas regulating valve. Indeed it has been seen above that the gas source S does not provide a solution for the breathing assistance device to be operated when the controlling means is disabled.

Therefore, when both the gas source and the controlling means are disabled, the breathing assistance device according to the invention is operated in the same way as when only the controlling means is disabled.

The reader will have understood that many modifications may be made without going beyond the new information and the advantages described herein. Consequently, all modifications of this type shall be within the scope of breathing assistance device and methods as defined in the attached claims.

The invention claimed is:

1. A breathing assistance device for a patient breathing in successive cycles, each cycle being defined by at least an inspiration phase and at least an expiration phase, said breathing assistance device including:

a source of respiratory pressurized gas, a gas transmission duct comprising a distal end coupled to said source and a proximal end coupled to said patient, a gas regulating valve comprising at least a leakage orifice between the inside and outside of said duct, and an obstruction means capable of varying the opening of said leakage orifice upon signal of a controlling means, wherein the gas regulating valve is interposed in said duct at a proximal location, and that the obstruction means is capable of allowing a bidirectional gas flow through said leakage orifice in both expiration and inspiration phases, wherein the breathing assistance device further comprises a return means comprising a magnetic equator, wherein the return means maintains the leakage orifice in an open position in the absence of a signal from the control means.

2. A breathing assistance device according to claim 1, wherein the obstruction means is electrically controlled.

3. A breathing assistance device according to claim 2, wherein the obstruction means is an electromagnetic obstruction means.

4. A breathing assistance device according to claim 1, wherein the electromagnetic obstruction means further comprises a metallic sheath wherein a coil is fixed, said coil being controllable by the controlling means and surrounding a movable magnetic element, the metallic sheath and the movable magnetic element defining the magnetic equator.

5. A breathing assistance device according to claim 4, wherein the magnetic element further comprises a toric magnet, a first polar piece and a second polar piece, said first and second polar pieces being coaxially fixed on either side of the toric magnet and being of different polarities, and said second polar piece comprising an obstruction piece being capable of obstructing the leakage orifice.

6. A breathing assistance device according to claim 5, wherein the magnetic element is translatable along an axis of revolution of the toric magnet.

7. A breathing assistance device according to claim 6, wherein the electromagnetic obstruction means includes two coaxial coils controllable by the controlling means, the first coil substantially surrounding the toric magnet and the first polar piece, and the second coil substantially surrounding the toric magnet and the second polar piece.

8. A breathing assistance device according to claim 7, wherein the electromagnetic obstruction means is mounted coaxially relative to the gas transmission duct.

9. A breathing assistance device according to claim 1, wherein the returns means is a compression spring.

10. A breathing assistance device according to claim 7, wherein the electromagnetic obstruction means includes an armature surrounded by a coil, said coil being controllable by the controlling means, and said armature comprising an inner toric space wherein a magnetic element is translatable.

11. A breathing assistance device according to claim 7, wherein the magnetic element is capable of obstructing the leakage orifice.

12. A breathing assistance device according to claim 10, wherein the magnetic element is constrained by a compression spring.

13. A breathing assistance device according to claim 10, wherein the magnetic element comprises a toric magnet and a magnet guide.

14. A breathing assistance device according to claim 13, characterized in that the electromagnetic obstruction means is mounted transverse to the gas transmission duct.

15. A breathing assistance method for assisting a patient with a breathing assistance device according claim 1, wherein the leakage orifice is at least partially opened in the absence of signal from the controlling means.

16. A breathing assistance method for assisting a patient according to claim 15, wherein the leakage orifice is totally obstructed during inspiration and at least partially opened during expiration.

17. A breathing assistance method for assisting a patient according to claim 16, wherein the leakage orifice, during expiration phases, is opened so that positive expiratory pressure remains equal to expiration pressure of the patient.

18. A breathing assistance method for assisting a patient according to claim 15, wherein the leakage orifice is totally opened in of the event the source of respiratory pressurized gas fails.

* * * * *